US012635627B2

(12) United States Patent
Aranda Regules et al.

(10) Patent No.: US 12,635,627 B2
(45) Date of Patent: May 26, 2026

(54) PLANTS RESISTANT TO INFECTION BY PEPINO MOSAIC VIRUS

(71) Applicants: ABIOPEP, S.L., Murcia (ES); CONSEJO SUPERIOR DE INVESTIGACIONES CIENTÍFICAS (CSIC), Madrid (ES)

(72) Inventors: Miguel A. Aranda Regules, Murcia (ES); Mª Pau Bretó Monfort, Murcia (ES); Fabiola Ruiz Ramón, Murcia (ES); Pascual Rodriguez Sepúlveda, Murcia (ES); Livia Donaire Segarra, Murcia (ES)

(73) Assignees: ABIOPEP, S.L., Murcia (ES); CONSEJO SUPERIOR DE INVESTIGACIONES CIENTÍFICAS (CSIC), Madrid (ES)

( * ) Notice: Subject to any disclaimer, the term of this patent is extended or adjusted under 35 U.S.C. 154(b) by 125 days.

(21) Appl. No.: 18/570,977

(22) PCT Filed: Jun. 16, 2022

(86) PCT No.: PCT/EP2022/066499
§ 371 (c)(1),
(2) Date: Dec. 15, 2023

(87) PCT Pub. No.: WO2022/263602
PCT Pub. Date: Dec. 22, 2022

(65) Prior Publication Data
US 2024/0276936 A1 Aug. 22, 2024

(30) Foreign Application Priority Data
Jun. 18, 2021 (ES) ................................ ES202130569

(51) Int. Cl.
| | |
|---|---|
| *A01H 1/00* | (2006.01) |
| *A01H 1/04* | (2006.01) |
| *A01H 1/06* | (2006.01) |
| *A01H 6/82* | (2018.01) |
| *C12Q 1/6895* | (2018.01) |

(52) U.S. Cl.
CPC ............. *A01H 1/126* (2021.01); *A01H 1/045* (2021.01); *A01H 1/06* (2013.01); *A01H 6/825* (2018.05); *C12Q 1/6895* (2013.01); *C12Q 2600/13* (2013.01)

(58) Field of Classification Search
None
See application file for complete search history.

(56) References Cited

U.S. PATENT DOCUMENTS

2010/0269224 A1 10/2010 Huang et al.
2014/0359836 A1* 12/2014 Wu ................... C12N 15/8274
536/23.6

FOREIGN PATENT DOCUMENTS

WO 2013064641 A1 5/2013

OTHER PUBLICATIONS

Fuji et al., *Arabidopsis* Vacuolar Sorting Mutants (green fluorescent seed) Can Be Identified Efficiently by Secretion of Vacuole-Targeted Green Fluorescent Protein in Their Seeds, 2007, The Plant Cell, 19:597-609 (Year: 2007).*
GenBank sequence of CSC-1 like Protein At4g35870 (Originally submitted on Mar. 10, 2000) (Year: 2016).*
Okano et al., Interfamily transfer of *Arabidopsis* lectin-mediated antiviral gene confers resistance to pepino mosaic virus in tomato, 2020, Journal of General Plant Pathology, 86:274-282 (Year: 2020).*
Yin et al., Genome-wide analysis of OSCA gene family members in Vigna radiata and their involvement in the osmotic response, BMC Plant Biology, 21:408 (Year: 2021).*
Ling et al. "Sources of Resistance to Pepino mosaic virus in Tomato Accessions", Article, 2007, vol. 91, No. 6, p. 749-753, Plant Disease.
Soler-Aleixandre et al. "Sources of Resistance to Pepino mosaic virus (PepMV) in Tomato", Article, 2007, vol. 42, No. 1, pp. 40-45, HortScience.
Candresse Thierry et al,. "Multiple Coat Protein Mutations Abolish Recognition of Pepino mosaic potexvirus (PepMV) by the Potato Rx Resistance Gene in Transgenic Tomatoes", Article, 2010, vol. 23, No. 4, pp. 376-383, Molecular Plant-Microbe Interactions.
Hyodo et al. "Hijacking of host cellular components as proviral factors by plant-infecting viruses", Article 2020, vol. 107, pp. 37-86, Advances in Virus Research, Elsevier.
Kourelis et al. "Defended to the Nines: 25 Years of Resistance Gene Cloning Identifies Nine Mechanisms for R Protein Function", Review, 2018, vol. 30, pp. 285-299, The Plant Cell.

(Continued)

*Primary Examiner* — Bratislav Stankovic
*Assistant Examiner* — Jay Chatterjee
(74) *Attorney, Agent, or Firm* — Hayes Soloway, PC

(57) ABSTRACT

The present invention relates to plants comprising in their genome a gene that has been inactivated rendering the plant resistant to Pepino mosaic virus (PepMV) infection. The present invention also refers to the inactivation of the gene required for PepMV infection. The invention encompasses parts of these plants and their progeny that show said gene inactivation and as a consequence an improved phenotype in terms of PepMV infection resistance. Methods for obtaining plants, or plant parts or seeds with resistance to PepMV infection are also part of this invention. The present invention further relates to the gene and sequences linked to it as markers for selecting plants resistant to PepMV infection. Therefore, the present invention belongs to the field of agriculture.

18 Claims, 9 Drawing Sheets
Specification includes a Sequence Listing.

(56)          References Cited

OTHER PUBLICATIONS

NICAISE "Crop immunity against viruses: outcomes and future challenges", Review Article, 2014, vol. 5, No. 660, 18 pages, Frontiers in Plant Science.

Truniger et al. "Recessive Resistance to Plant Viruses" Article, 2009, vol. 75, 43 Pages, Advances in Virus Research.

Soler et al. "New sources of resistance to PepMV in tomato", Article, 2011, vol. 118, No. 5, pp. 149-155, Journal of Plant Diseases and Protection.

Mathioudakis et al. "Multifaceted Capsid Proteins: Multiple Interactions Suggest Multiple Roles for Pepino mosaic virus Capsid Protein", Article, 2014, vol. 27, No. 12, pp. 1356-1369, Molecular Plant-Microbe Interactions.

Makinen "Plant susceptibility genes as a source for potyvirus resistance", Article, 2020, vol. 176, Issue 2, pp. 122-129, Annals of Applied Biology.

Gomez et al. "Mixed Infections of Pepino Mosaic Virus Strains Modulate the Evolutionary Dynamics of this Emergent Virus", Article, 2009, vol. 83, No. 23, pp. 12378-12387, Journal of Virology.

Aguero et al. "Stable and Broad Spectrum Cross-Protection Against Pepino Mosaic Virus Attained by Mixed Infection", Article, 2018, vol. 9, No. 1810, 12 Pages, Frontiers in Plant Science.

Marco et al. "Melon Resistance to Cucurbit yellow stunting disorder virus Is Characterized by Reduced Virus Accumulation", 2003, vol. 93, No. 7, pp. 844-852, Phytopathology.

Li et al. "Fast and accurate short read alignment with Burrows-Wheeler transform", Paper, 2009, vol. 25, No. 14, pp. 1754-1760, Bioinformatics.

Bolger et al. "The genome of the stress-tolerant wild tomato species *Solanum pennellii*", Letter, 2014. vol. 46, No. 9. pp. 1034-1039, Nature Genetics.

Cingolani et al. "A program for annotating and predicting the effects of single nucleotide polymorphisms, SnpEff: SNPs in the genome of *Drosophila melanogaster* strain w1118; iso-2; iso-3", Article, 2012, vol. 6, No. 2, pp. 80-92, Fly(Austin), Landes Bioscience.

Cermak et al. "A Multipurpose Toolkit to Enable Advanced Genome Engineering in Plants", Article, 2017, vol. 29, pp. 1196-1217, The Plant Cell.

Van Eck et al. "Tomato (*Lycopersicum esculentum*)", Protocol, 2006, vol. 343, pp. 459-484, Agrobacterium Protocols, Methods Molecular Biology.

Zhu et al. "Integrating Large-Scale Functional Genomic Data to Dissect the Complexity of Yeast Regulatory Networks", Manuscript, 2008, vol. 40, No. 7, pp. 854-861, Nat. Genet.

Yuan et al. "OSCA1 mediates osmotic-stress-evoked Ca2+ increases vital for osmosensing in *Arabidopsis*", Letter, 2014, vol. 514, 18 Pages, Nature.

Delgadillo et al. "MTV proteins unveil ER- and microtubule-associated compartments in the plant vacuolar trafficking pathway", Article, 2020, vol. 117, No. 18, pp. 9884-9895, PNAS.

Tan et al. "Regeneration of leaf mesophyll protoplasts of tomato cultivars (*L. esculentum*): factors important for efficient protoplast culture and plant regeneration", Article, 1987, vol. 6, pp. 172-175, Plant Cell Reports, Springer-Verlag.

Bolger et al. "Trimmomatic: a flexible trimmer for Illumina sequence data", Paper, 2014, vol. 30, No. 15, pp. 2114-2120, Bioinformatics.

Fuji et al. "*Arabidopsis* Vacuolar Sorting Mutants (green fluorescent seed) Can Be Identified Efficiently by Secretion of Vacuole-Targeted Green Fluorescent Protein in Their Seeds", Article, 2007, vol. 19, pp. 597-609, The Plant Cell.

Oliveros et al. "Breaking-Cas—interactive design of guide RNAs for CRISPR-Cas experiments for ENSEMBL genomes", Article, 2016, vol. 44, pp. W267-W271, Nucleic Acids Research.

Garrison et al. "Haplotype-based variant detection from short-read sequencing", Paper, 2012, pp. 1-9, ArXiv, Quantitative Biology, Genomics.

* cited by examiner

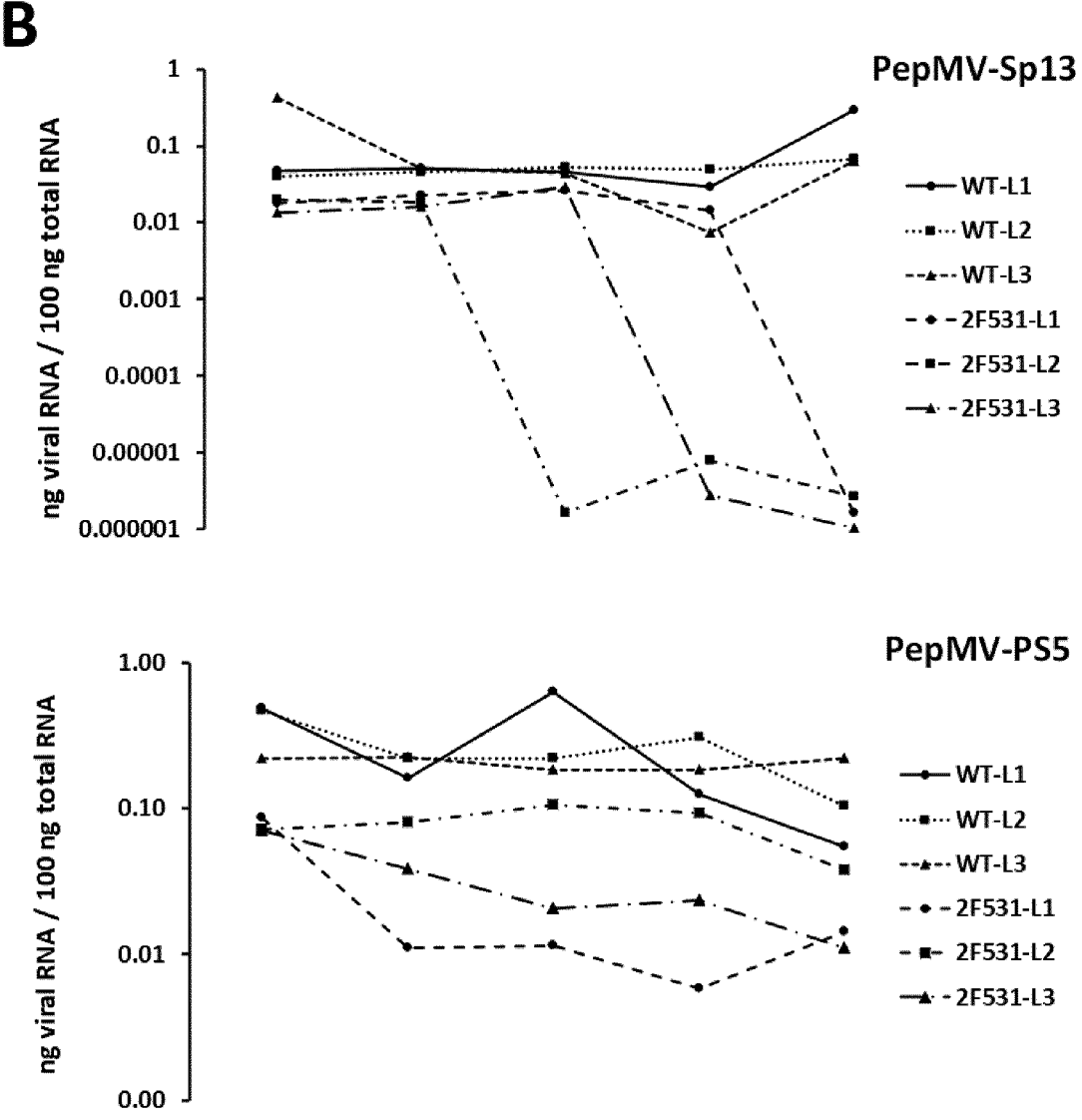
FIG. 3 (CONTINUATION)

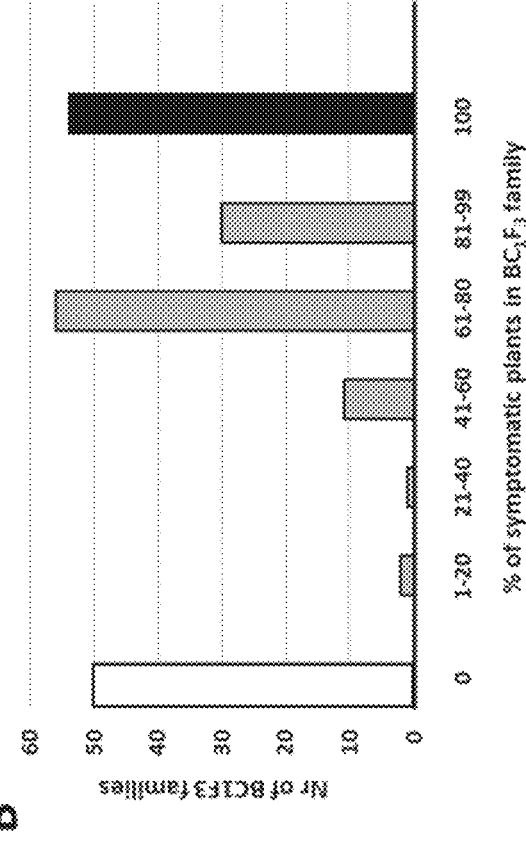
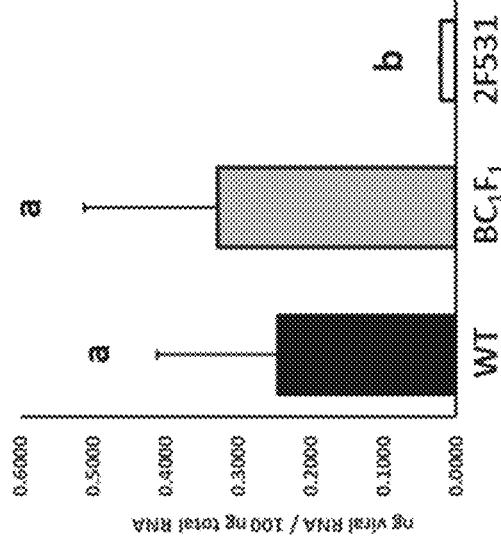
FIG. 4

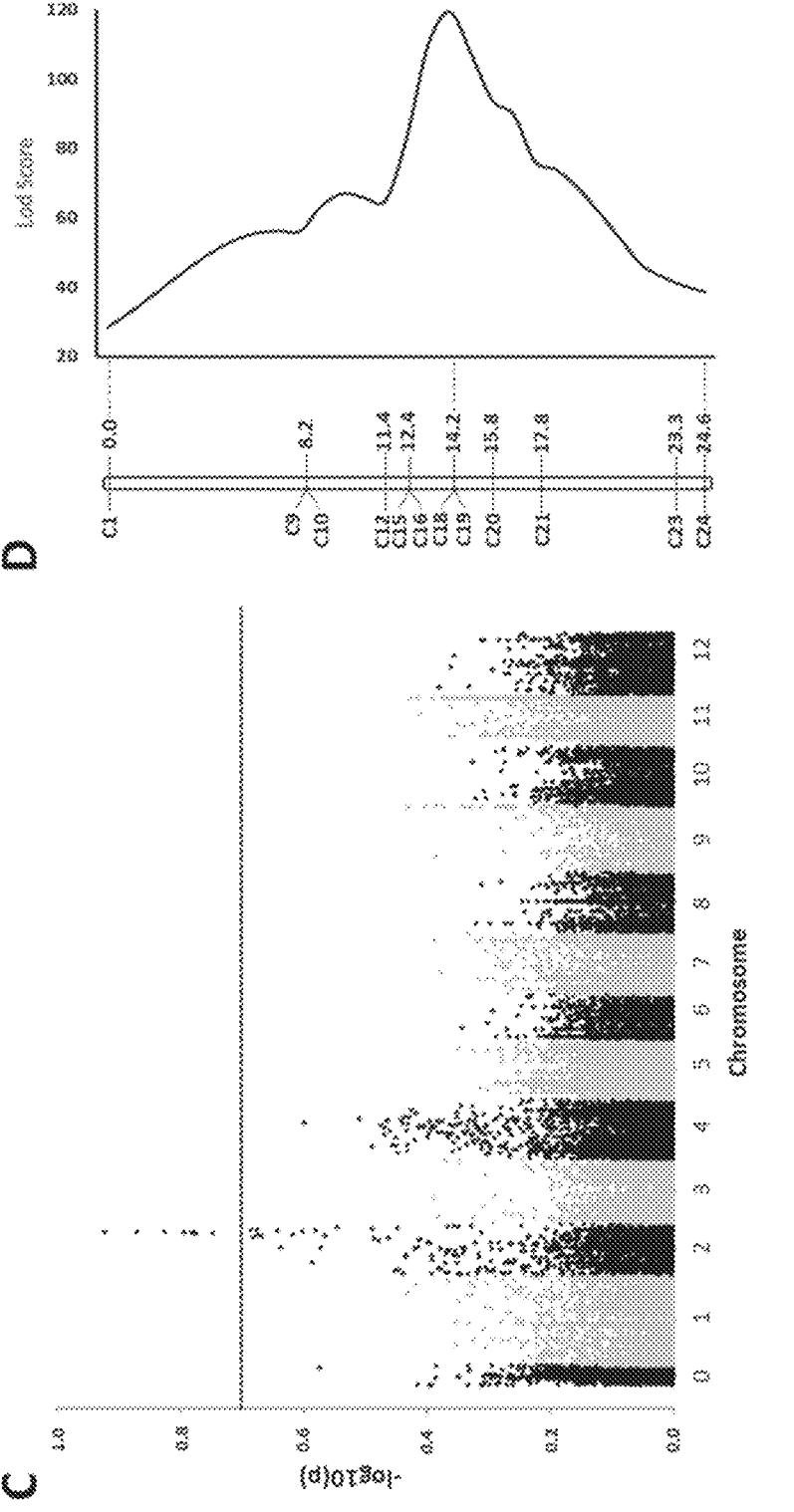
FIG. 4 (CONTINUATION)

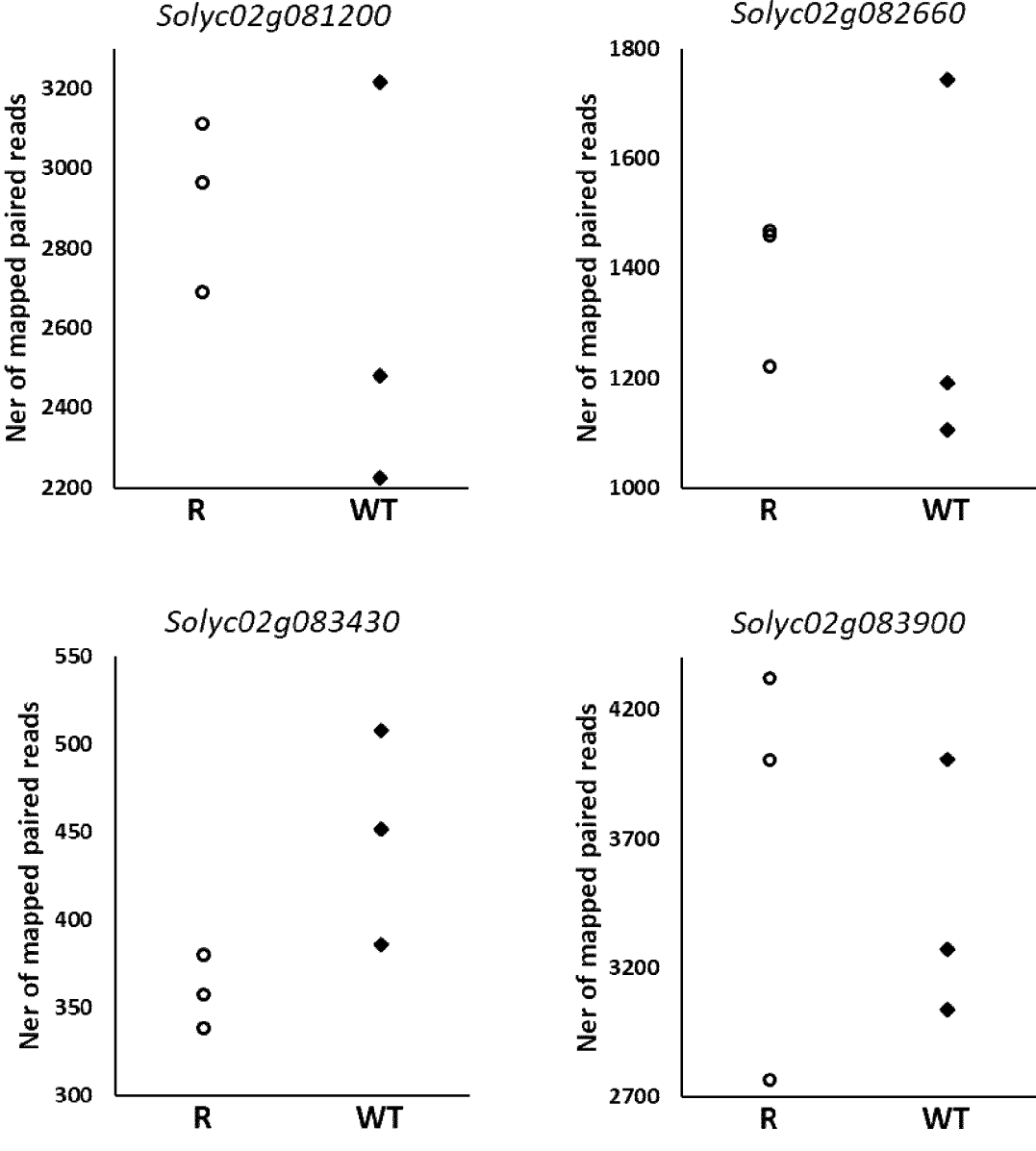
FIG: 5

A
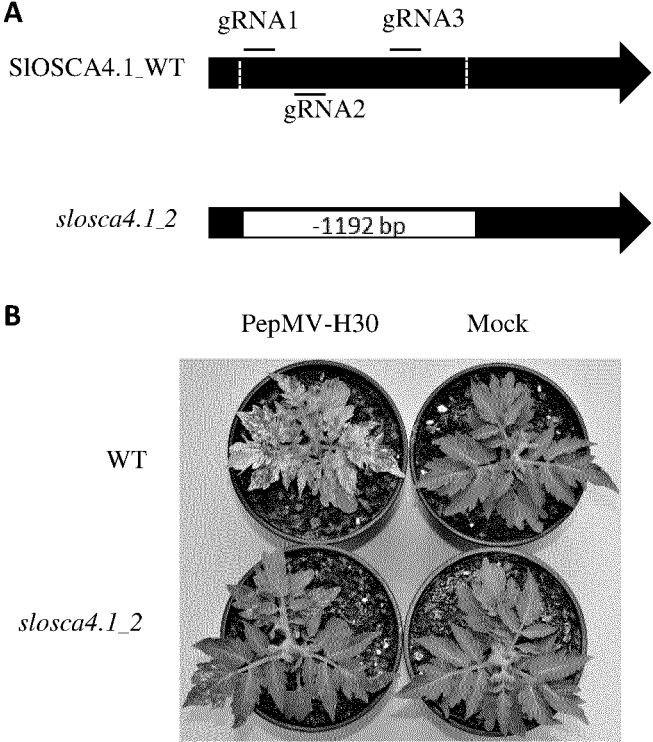
B
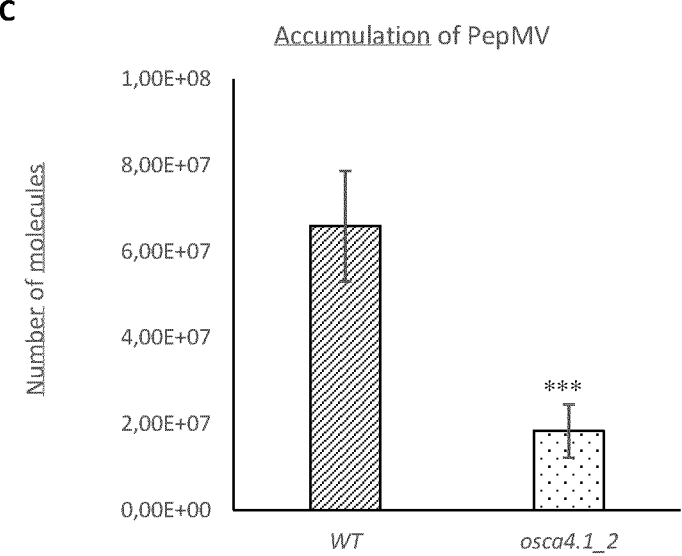
C
Accumulation of PepMV
FIG. 6

SEQUENCE LISTING

```
<160> NUMBER OF SEQ ID NOS: 9

<210> SEQ ID NO 1
<211> LENGTH: 831
<212> TYPE: PRT
<213> ORGANISM: Solanum lycopersicum

<400> SEQUENCE: 1

Met Ile Gln Ser Ser Phe Ser Ala Asp Ser Pro Ser Met Ala Ala Asn
1               5                   10                  15

Ser Thr Phe Ser Pro Pro Pro Ala Ala Gly Asp Gly Asp Phe Asn Tyr
                20              25                  30

Asp Val Ala Trp Tyr Gly Asn Ile Gln Tyr Leu Leu Asn Ile Ser Ala
            35              40                  45

Ile Gly Ala Leu Thr Cys Leu Leu Ile Phe Ile Phe Gly Lys Leu Arg
        50              55                  60

Ser Asp His Arg Arg Met Pro Gly Pro Thr Ala Ile Val Ser Lys Leu
65              70                  75                  80

Leu Ala Ala Trp His Ala Thr Gly Val Glu Ile Ala Arg His Cys Gly
                85                  90                  95

Ala Asp Ala Ala Gln Tyr Leu Leu Ile Glu Gly Gly Ser Ser Ala Leu
            100                 105                 110

Leu Leu Phe Leu Ala Leu Leu Ser Leu Ala Val Met Leu Pro Leu Asn
        115                 120                 125

Ile Tyr Ala Gly Lys Ala Pro Met Ala Asp Gln Phe Ser Lys Thr Thr
    130                 135                 140

Ile Asn His Ile Glu Lys Gly Ser Pro Leu Leu Trp Ile His Phe Ile
145                 150                 155                 160

Phe Val Val Ile Val Val Val Leu Val His Tyr Gly Ile Ser Glu Ile
                165                 170                 175

Gln Glu Arg Leu Lys Ile Thr Arg Leu Arg Asp Gly Tyr Gly Asn Pro
            180                 185                 190

Ser Asn Ser Gly Thr Asn Val Ser Ala Ile Phe Ser Ile Met Val Gln
            195                 200                 205

Gly Val Pro Lys Thr Leu Gly Phe Asp Lys Thr Pro Leu Val Glu Tyr
    210                 215                 220

Phe Gln His Lys Tyr Pro Gly Lys Val Tyr Arg Val Val Val Pro Met
```

-continued

```
225                 230                 235                 240

Asp Leu Cys Ala Leu Asp Asp Leu Ala Thr Glu Leu Val Lys Val Arg
            245             250             255

Glu Asp Ile Ser Lys Leu Val Ser Arg Ile Glu Leu Arg Gly Tyr Leu
            260             265             270

Asn Glu Gly Glu Glu Asp Glu Tyr Asn Asn Asp Ser Val Asn Gly Arg
            275             280             285

Gly Leu Leu Glu Arg Leu Cys Phe Leu Trp Arg Lys Ala Lys Asp Thr
        290             295             300

Trp Tyr His Val Val Asp Gln Leu Gly Phe Ser Asp Glu Glu Arg Leu
    305             310             315             320

Arg Lys Leu Gln Glu Leu Arg Ala Asp Leu Glu Met Glu Met Ala Ser
            325             330             335

Tyr Lys Glu Gly Arg Ala Arg Gly Ala Gly Val Ala Phe Val Val Phe
            340             345             350

Lys Asp Val Phe Thr Ala Asn Lys Ala Val Gln Asp Leu Arg Asn Glu
            355             360             365

Lys Arg Arg Arg Tyr Gly Arg Phe Phe Ser Val Ile Glu Leu Gln Leu
        370             375             380

Gln Arg Asn Gln Trp Lys Val Glu Arg Ala Pro Leu Ala Thr Asp Ile
    385             390             395             400

Tyr Trp Asn His Leu Gly Ser Thr Lys Phe Ser Leu Lys Leu Arg Arg
            405             410             415

Val Leu Val Asn Thr Cys Leu Leu Leu Met Leu Leu Phe Cys Ser Ser
            420             425             430

Pro Leu Ala Val Ile Ser Ala Ile Gln Ser Ala Gly Arg Ile Ile Asn
        435             440             445

Ala Glu Ala Met Asp His Ala Gln Met Trp Leu Asn Trp Val Gln Gly
        450             455             460

Ser Ser Trp Leu Ala Thr Ile Ile Phe Gln Phe Leu Pro Asn Val Leu
465             470             475             480

Ile Phe Val Ser Met Tyr Ile Val Val Pro Ser Val Leu Ser Tyr Leu
            485             490             495

Ser Lys Phe Glu Gln His Leu Thr Val Ser Gly Glu Gln Arg Ala Glu
            500             505             510

Leu Leu Lys Met Val Cys Phe Phe Leu Val Asn Leu Ile Leu Leu Arg
        515             520             525

Ala Leu Val Glu Ser Thr Leu Glu Gly Ala Leu Leu Ser Met Gly Arg
        530             535             540

Cys Tyr Leu Asp Gly Glu Asp Cys Lys Lys Ile Glu Gln Tyr Met Thr
545             550             555             560

Ala Ser Phe Leu Thr Arg Thr Cys Leu Ser Ser Leu Ala Phe Leu Ile
            565             570             575

Thr Ser Ser Phe Leu Gly Ile Ser Phe Asp Leu Leu Ala Pro Ile Pro
            580             585             590

Trp Ile Lys Lys Lys Leu Gln Lys Phe Arg Lys Asn Asp Met Leu Gln
        595             600             605

Leu Val Pro Glu Arg Ser Glu Glu Tyr Pro Leu Glu Asn Gln Asp Ile
        610             615             620

Asp Ser Leu Glu Arg Pro Leu Ile His Glu Arg Ser Ser Thr Val Ile
625             630             635             640

Ala Asp Asn Asn Gly Phe Leu His Asp Ala Ser Pro Asn Glu Ile Asp
            645             650             655
```

```
Phe Pro Gly Gln Asp Leu Ser Glu Tyr Pro Pro Val Ser Arg Thr Ser
            660             665             670

Pro Val Pro Lys Pro Lys Phe Asp Phe Ala Gln Tyr Tyr Ala Phe Asn
            675             680             685

Leu Thr Ile Phe Ala Leu Thr Leu Ile Tyr Cys Ser Phe Ala Pro Leu
            690             695             700

Val Val Pro Val Gly Ala Val Tyr Phe Gly Tyr Arg Tyr Leu Val Asp
705             710             715             720

Lys Tyr Asn Phe Leu Phe Val Tyr Arg Val Arg Gly Phe Pro Ala Gly
            725             730             735

Asn Asp Gly Arg Leu Met Asp Thr Val Leu Ser Ile Met Arg Phe Cys
            740             745             750

Val Asp Leu Phe Leu Leu Ser Met Leu Leu Phe Phe Ser Val Arg Gly
            755             760             765

Asp Ser Thr Lys Leu Gln Ala Ile Phe Thr Leu Gly Leu Leu Val Val
            770             775             780

Tyr Lys Leu Leu Pro Ser Asp Lys Asp Ser Phe Gln Pro Ala Leu Leu
785             790             795             800

Gln Gly Ile Gln Thr Ile Asp Asn Ile Val Glu Gly Pro Thr Asp Tyr
            805             810             815

Glu Val Phe Ser Gln Pro Thr Phe Asp Trp Asp Thr Tyr Asn Ser
            820             825             830

<210> SEQ ID NO 2
<211> LENGTH: 553
<212> TYPE: PRT
<213> ORGANISM: Artificial Sequence
<220> FEATURE:
<223> OTHER INFORMATION: EMS mutant

<400> SEQUENCE: 2

Met Ile Gln Ser Ser Phe Ser Ala Asp Ser Pro Ser Met Ala Ala Asn
1               5               10              15

Ser Thr Phe Ser Pro Pro Ala Ala Gly Asp Gly Asp Phe Asn Tyr
            20              25              30

Asp Val Ala Trp Tyr Gly Asn Ile Gln Tyr Leu Leu Asn Ile Ser Ala
            35              40              45

Ile Gly Ala Leu Thr Cys Leu Leu Ile Phe Ile Phe Gly Lys Leu Arg
    50              55              60

Ser Asp His Arg Arg Met Pro Gly Pro Thr Ala Ile Val Ser Lys Leu
65              70              75              80

Leu Ala Ala Trp His Ala Thr Gly Val Glu Ile Ala Arg His Cys Gly
            85              90              95

Ala Asp Ala Ala Gln Tyr Leu Leu Ile Glu Gly Gly Ser Ser Ala Leu
            100             105             110

Leu Leu Phe Leu Ala Leu Leu Ser Leu Ala Val Met Leu Pro Leu Asn
            115             120             125

Ile Tyr Ala Gly Lys Ala Pro Met Ala Asp Gln Phe Ser Lys Thr Thr
            130             135             140

Ile Asn His Ile Glu Lys Gly Ser Pro Leu Leu Trp Ile His Phe Ile
145             150             155             160

Phe Val Val Ile Val Val Val Leu Val His Tyr Gly Ile Ser Glu Ile
            165             170             175

Gln Glu Arg Leu Lys Ile Thr Arg Leu Arg Asp Gly Tyr Gly Asn Pro
            180             185             190
```

Ser Asn Ser Gly Thr Asn Val Ser Ala Ile Phe Ser Ile Met Val Gln
        195                 200                 205

Gly Val Pro Lys Thr Leu Gly Phe Asp Lys Thr Pro Leu Val Glu Tyr
        210                 215                 220

Phe Gln His Lys Tyr Pro Gly Lys Val Tyr Arg Val Val Val Pro Met
225                 230                 235                 240

Asp Leu Cys Ala Leu Asp Asp Leu Ala Thr Glu Leu Val Lys Val Arg
                245                 250                 255

Glu Asp Ile Ser Lys Leu Val Ser Arg Ile Glu Leu Arg Gly Tyr Leu
                260                 265                 270

Asn Glu Gly Glu Glu Asp Glu Tyr Asn Asn Asp Ser Val Asn Gly Arg
                275                 280                 285

Gly Leu Leu Glu Arg Leu Cys Phe Leu Trp Arg Lys Ala Lys Asp Thr
        290                 295                 300

Trp Tyr His Val Val Asp Gln Leu Gly Phe Ser Asp Glu Glu Arg Leu
305                 310                 315                 320

Arg Lys Leu Gln Glu Leu Arg Ala Asp Leu Glu Met Glu Met Ala Ser
                325                 330                 335

Tyr Lys Glu Gly Arg Ala Arg Gly Ala Gly Val Ala Phe Val Val Phe
                340                 345                 350

Lys Asp Val Phe Thr Ala Asn Lys Ala Val Gln Asp Leu Arg Asn Glu
                355                 360                 365

Lys Arg Arg Arg Tyr Gly Arg Phe Phe Ser Val Ile Glu Leu Gln Leu
        370                 375                 380

Gln Arg Asn Gln Trp Lys Val Glu Arg Ala Pro Leu Ala Thr Asp Ile
385                 390                 395                 400

Tyr Trp Asn His Leu Gly Ser Thr Lys Phe Ser Leu Lys Leu Arg Arg
                405                 410                 415

Val Leu Val Asn Thr Cys Leu Leu Leu Met Leu Leu Phe Cys Ser Ser
                420                 425                 430

Pro Leu Ala Val Ile Ser Ala Ile Gln Ser Ala Gly Arg Ile Ile Asn
        435                 440                 445

Ala Glu Ala Met Asp His Ala Gln Met Trp Leu Asn Trp Val Gln Gly
        450                 455                 460

Ser Ser Trp Leu Ala Thr Ile Ile Phe Gln Phe Leu Pro Asn Val Leu
465                 470                 475                 480

Ile Phe Val Ser Met Tyr Ile Val Val Pro Ser Val Leu Ser Tyr Leu
                485                 490                 495

Ser Lys Phe Glu Gln His Leu Thr Val Ser Gly Glu Gln Arg Ala Glu
                500                 505                 510

Leu Leu Lys Met Val Cys Phe Phe Leu Val Asn Leu Ile Leu Leu Arg
        515                 520                 525

Ala Leu Val Glu Ser Thr Leu Glu Gly Ala Leu Leu Ser Met Gly Arg
        530                 535                 540

Cys Tyr Leu Asp Gly Glu Asp Cys Lys
545                 550

<210> SEQ ID NO 3
<211> LENGTH: 434
<212> TYPE: PRT
<213> ORGANISM: Artificial Sequence
<220> FEATURE:
<223> OTHER INFORMATION: CRISPR/Cas9 mutant

<400> SEQUENCE: 3

```
Met Ile Gln Ser Ser Phe Ser Ala Asp Ser Gln Lys Phe Ser Leu Lys
1               5                   10                  15

Leu Arg Arg Val Leu Val Asn Thr Cys Leu Leu Leu Met Leu Leu Phe
            20                  25                  30

Cys Ser Ser Pro Leu Ala Val Ile Ser Ala Ile Gln Ser Ala Gly Arg
        35                  40                  45

Ile Ile Asn Ala Glu Ala Met Asp His Ala Gln Met Trp Leu Asn Trp
    50                  55                  60

Val Gln Gly Ser Ser Trp Leu Ala Thr Ile Ile Phe Gln Phe Leu Pro
65                  70                  75                  80

Asn Val Leu Ile Phe Val Ser Met Tyr Ile Val Val Pro Ser Val Leu
                85                  90                  95

Ser Tyr Leu Ser Lys Phe Glu Gln His Leu Thr Val Ser Gly Glu Gln
            100                 105                 110

Arg Ala Glu Leu Leu Lys Met Val Cys Phe Phe Leu Val Asn Leu Ile
        115                 120                 125

Leu Leu Arg Ala Leu Val Glu Ser Thr Leu Glu Gly Ala Leu Leu Ser
    130                 135                 140

Met Gly Arg Cys Tyr Leu Asp Gly Glu Asp Cys Lys Lys Ile Glu Gln
145                 150                 155                 160

Tyr Met Thr Ala Ser Phe Leu Thr Arg Thr Cys Leu Ser Ser Leu Ala
                165                 170                 175

Phe Leu Ile Thr Ser Ser Phe Leu Gly Ile Ser Phe Asp Leu Leu Ala
            180                 185                 190

Pro Ile Pro Trp Ile Lys Lys Lys Leu Gln Lys Phe Arg Lys Asn Asp
        195                 200                 205

Met Leu Gln Leu Val Pro Glu Arg Ser Glu Glu Tyr Pro Leu Glu Asn
    210                 215                 220

Gln Asp Ile Asp Ser Leu Glu Arg Pro Leu Ile His Glu Arg Ser Ser
225                 230                 235                 240

Thr Val Ile Ala Asp Asn Asn Gly Phe Leu His Asp Ala Ser Pro Asn
                245                 250                 255

Glu Ile Asp Phe Pro Gly Gln Asp Leu Ser Glu Tyr Pro Pro Val Ser
            260                 265                 270

Arg Thr Ser Pro Val Pro Lys Pro Lys Phe Asp Phe Ala Gln Tyr Tyr
        275                 280                 285

Ala Phe Asn Leu Thr Ile Phe Ala Leu Thr Leu Ile Tyr Cys Ser Phe
    290                 295                 300

Ala Pro Leu Val Val Pro Val Gly Ala Val Tyr Phe Gly Tyr Arg Tyr
305                 310                 315                 320

Leu Val Asp Lys Tyr Asn Phe Leu Phe Val Tyr Arg Val Arg Gly Phe
                325                 330                 335

Pro Ala Gly Asn Asp Gly Arg Leu Met Asp Thr Val Leu Ser Ile Met
            340                 345                 350

Arg Phe Cys Val Asp Leu Phe Leu Leu Ser Met Leu Leu Phe Phe Ser
        355                 360                 365

Val Arg Gly Asp Ser Thr Lys Leu Gln Ala Ile Phe Thr Leu Gly Leu
    370                 375                 380

Leu Val Val Tyr Lys Leu Leu Pro Ser Asp Lys Asp Ser Phe Gln Pro
385                 390                 395                 400

Ala Leu Leu Gln Gly Ile Gln Thr Ile Asp Asn Ile Val Glu Gly Pro
                405                 410                 415
```

```
Thr Asp Tyr Glu Val Phe Ser Gln Pro Thr Phe Asp Trp Asp Thr Tyr
        420                 425                 430

Asn Ser

<210> SEQ ID NO 4
<211> LENGTH: 2496
<212> TYPE: DNA
<213> ORGANISM: Solanum lycopersicum

<400> SEQUENCE: 4
atgatccaat ccagcttctc tgcagactca ccttccatgg cagccaattc cactttctct      60
cctccgccgg ccgccggtga cggagacttc aattacgacg tcgcttggta tggtaacatc     120
cagtacctcc tcaatatctc cgccattgga gctttgactt gccttcttat tttcatcttc     180
gggaagcttc gaagcgacca ccgtcgcatg cccggtccca ctgccattgt ctccaagctc     240
ttagctgcct ggcacgccac tggtgttgaa atcgcccgcc actgcggggc tgacgctgct     300
caatatctcc ttattgaggg cggcagctct gccctgctat tattcctcgc ccttctttct     360
cttgctgtaa tgctgccgtt gaatatatat gctggtaagg ctcctatggc tgatcagttt     420
tcaaagacta caataaacca tatagaaaaa ggttctccat tactctggat tcactttata     480
tttgttgtta ttgttgttgt tttggtacat tatggtataa gtgaaataca agaaaggttg     540
aaaattacta gacttagaga cggctatgga aatccgagta attctggtac aaatgtcagt     600
gcaatttttt ccattatggt gcagggtgta cctaagacct taggttttga taagacacct     660
ttagtggagt attttcagca taaatatccg gggaaggtgt atagagtagt tgtccctatg     720
gatttgtgtg ctctggatga tttagctaca gagttggtga aggttcggga agatatctct     780
aaactagtct caagaattga gttacggggt tatttgaatg agggtgagga agacgagtat     840
aataatgata gtgtgaacgg gcggggcttg ttagaacgac tgtgcttttt gtggagaaag     900
gctaaggata catggtatca tgttgtggat caattaggtt ctcagatga agagagatta      960 agaaaattgc aagagttgag agctgatttg gagatggaaa tggcatctta taagaaggg    1020 agggcaagag gtgctggtgt agcttttgtg gtatttaagg acgtattcac agctaataag    1080
gctgtccagg acctccggaa tgagaagagg aggcgatatg gtcgattctt ctcagtcatt    1140
gagttgcaac tacagaggaa ccagtggaaa gtggagagag ctcctttagc tactgacata    1200
tactggaacc acctgggatc aacaaagttc tccttaaagc tgcgcagagt gttggtgaac    1260
acatgcctat tgttgatgtt gctattctgc agttctccac tagctgtgat tagtgctatt    1320
caaagtgcag ggagaataat caatgctgaa gctatggatc atgctcagat gtggctgaac    1380
tgggtgcagg gctcgagctg ctagcaaca ataatatttc aatttttgcc caatgttctg     1440
atttttgtga gcatgtacat tgttgtccct tcagttcttt cttatctttc taaatttgaa    1500
caacatctta ctgtatctgg tgagcaaagg gctgagctac tgaaaatggt ttgcttcttt    1560
ctggtaaatc tcattctgct tagggctctg gtcgaatcta ctcttgaggg tgctctctta    1620
agtatgggtc ggtgttattt ggatggagaa gattgcaaaa agatcgagca gtacatgact    1680 gcttccttt tgacaaggac atgcctctcg tctcttgcat tttaattac aagcagtttt      1740 ttgggtatat cttttgattt attagctcca attccttgga ttaagaagaa gcttcaaaag    1800
ttccgtaaaa atgacatgct tcagttggta ccagaacgga gtgaggagta cccattggaa    1860
aatcaagaca ttgatagttt ggagaggcct ctgattcatg aaaggagttc aactgtgatt    1920
gctgacaaca atggattttt acacgatgcc tctccaaatg aaattgattt ccctggacaa    1980
```

-continued

```
gatttgtctg aataccctcc agtcagccga acctcaccag ttccaaagcc gaagtttgat    2040
tttgcacagt attatgcttt caatctgaca atatttgccc taaccctgat ctattgttcg    2100
tttgctcctc tggtggttcc tgttggtgca gtttactttg ggtaccggta tttagttgac    2160
aagtacaact tcctgtttgt atacagagtg cgaggtttcc ctgctggtaa tgatgggagg    2220
ttgatggata ctgtattatc tatcatgagg ttttgtgttg acttgttcct cctttcaatg    2280
ctacttttct tttctgtacg aggagactca actaagcttc aagccatatt cacacttgga    2340
ttgttagtgg tgtataaact cttgccctct gataaggatt cttttcagcc agcgttatta    2400
caaggcatac agactattga caacattgtc gaagggccaa ctgattatga ggttttctca    2460
caacctacat ttgattggga tacgtataat tcatga                             2496
```

```
<210> SEQ ID NO 5
<211> LENGTH: 2496
<212> TYPE: DNA
<213> ORGANISM: Artificial Sequence
<220> FEATURE:
<223> OTHER INFORMATION: EMS mutant

<400> SEQUENCE: 5
```

```
atgatccaat ccagcttctc tgcagactca ccttccatgg cagccaattc cactttctct     60
cctccgccgg ccgccggtga cggagacttc aattacgacg tcgcttggta tggtaacatc    120
cagtacctcc tcaatatctc cgccattgga gctttgactt gccttcttat tttcatcttc    180
gggaagcttc gaagcgacca ccgtcgcatg cccggtccca ctgccattgt ctccaagctc    240
ttagctgcct ggcacgccac tggtgttgaa atcgcccgcc actgcggggc tgacgctgct    300
caatatctcc ttattgaggg cggcagctct gccctgctat tattcctcgc ccttctttct    360
cttgctgtaa tgctgccgtt gaatatatat gctggtaagg ctcctatggc tgatcagttt    420
tcaaagacta caataaacca tatagaaaaa ggttctccat tactctggat tcactttata    480
tttgttgtta ttgttgttgt tttggtacat tatggtataa gtgaaataca agaaaggttg    540
aaaattacta gacttagaga cggctatgga aatccgagta attctggtac aaatgtcagt    600
gcaatttttt ccattatggt gcagggtgta cctaagacct taggttttga taagacacct    660
ttagtggagt attttcagca taaatatccg gggaaggtgt atagagtagt tgtccctatg    720
gatttgtgtg ctctggatga tttagctaca gagttggtga aggttcggga agatatctct    780
aaactagtct caagaattga gttacggggt tatttgaatg agggtgagga agacgagtat    840
aataatgata gtgtgaacgg gcggggcttg ttagaacgac tgtgcttttt gtggagaaag    900
gctaaggata catggtatca tgttgtggat caattaggtt tctcagatga agagagatta    960
agaaaattgc aagagttgag agctgatttg gagatggaaa tggcatctta taaagaaggg   1020
agggcaagag gtgctggtgt agcttttgtg gtatttaagg acgtattcac agctaataag   1080
gctgtccagg acctccggaa tgagaagagg aggcgatatg gtcgattctt ctcagtcatt   1140
gagttgcaac tacagaggaa ccagtggaaa gtggagagag ctcctttagc tactgacata   1200
tactggaacc acctgggatc aacaaagttc tccttaaagc tgcgcagagt gttggtgaac   1260
acatgcctat tgttgatgtt gctattctgc agttctccac tagctgtgat tagtgctatt   1320
caaagtgcag ggagaataat caatgctgaa gctatggatc atgctcagat gtggctgaac   1380
tgggtgcagg gctcgagctg gctagcaaca ataatatttc aatttttgcc caatgttctg   1440 attttttgtga gcatgtacat tgttgtccct tcagttcttt cttatctttc taaatttgaa   1500
caacatctta ctgtatctgg tgagcaaagg gctgagctac tgaaaatggt ttgcttcttt   1560
```

```
ctggtaaatc tcattctgct tagggctctg gtcgaatcta ctcttgaggg tgctctctta      1620
agtatgggtc ggtgttattt ggatggagaa gattgcaaat agatcgagca gtacatgact      1680
gcttcctttt tgacaaggac atgcctctcg tctcttgcat ttttaattac aagcagtttt      1740
ttgggtatat cttttgattt attagctcca attccttgga ttaagaagaa gcttcaaaag      1800
ttccgtaaaa atgacatgct tcagttggta ccagaacgga gtgaggagta cccattggaa      1860
aatcaagaca ttgatagttt ggagaggcct ctgattcatg aaaggagttc aactgtgatt      1920
gctgacaaca atggattttt acacgatgcc tctccaaatg aaattgattt ccctggacaa      1980
gatttgtctg aataccctcc agtcagccga acctcaccag ttccaaagcc gaagtttgat      2040
tttgcacagt attatgcttt caatctgaca atatttgccc taaccctgat ctattgttcg      2100
tttgctcctc tggtggttcc tgttggtgca gtttactttg ggtaccggta tttagttgac      2160
aagtacaact tcctgtttgt atacagagtg cgaggtttcc ctgctggtaa tgatgggagg      2220
ttgatggata ctgtattatc tatcatgagg ttttgtgttg acttgttcct cctttcaatg      2280
ctacttttct tttctgtacg aggagactca actaagcttc aagccatatt cacacttgga      2340
ttgttagtgg tgtataaact cttgccctct gataaggatt cttttcagcc agcgttatta      2400
caaggcatac agactattga caacattgtc gaagggccaa ctgattatga ggttttctca      2460
caacctacat ttgattggga tacgtataat tcatga                                2496

<210> SEQ ID NO 6
<211> LENGTH: 1305
<212> TYPE: DNA
<213> ORGANISM: Artificial Sequence
<220> FEATURE:
<223> OTHER INFORMATION: CRISPR/Cas9 mutant

<400> SEQUENCE: 6
atgatccaat ccagcttctc tgcagactca caaaagttct ccttaaagct gcgcagagtg        60
ttggtgaaca catgcctatt gttgatgttg ctattctgca gttctccact agctgtgatt       120
agtgctattc aaagtgcagg gagaataatc aatgctgaag ctatggatca tgctcagatg       180
tggctgaact gggtgcaggg ctcgagctgg ctagcaacaa taatatttca atttttgccc       240
aatgttctga tttttgtgag catgtacatt gttgtccctt cagttctttc ttatctttct       300
aaatttgaac aacatcttac tgtatctggt gagcaaaggg ctgagctact gaaaatggtt       360
tgcttctttc tggtaaatct cattctgctt agggctctgg tcgaatctac tcttgagggt       420
gctctcttaa gtatgggtcg tgttatttg atggagaag attgcaaaaa gatcgagcag       480
tacatgactg cttccttttt gacaaggaca tgcctctcgt ctcttgcatt tttaattaca       540
agcagttttt tgggtatatc ttttgattta ttagctccaa ttccttggat taagaagaag       600
cttcaaaagt tccgtaaaaa tgacatgctt cagttggtac agaacggag tgaggagtac        660 ccattggaaa atcaagacat tgatagtttg gagaggcctc tgattcatga aaggagttca       720
actgtgattg ctgacaacaa tggatttttta cacgatgcct ctccaaatga aattgatttc       780
cctggacaag atttgtctga ataccctcca gtcagccgaa cctcaccagt tccaaagccg       840
aagtttgatt ttgcacagta ttatgctttc aatctgacaa tatttgccct aaccctgatc       900
tattgttcgt ttgctcctct ggtggttcct gttggtgcag tttactttgg gtaccggtat       960
ttagttgaca agtacaactt cctgtttgta tacagagtgc gaggtttccc tgctggtaat      1020
gatgggaggt tgatggatac tgtattatct atcatgaggt tttgtgttga cttgttcctc      1080
```

-continued

```
ctttcaatgc tacttttctt ttctgtacga ggagactcaa ctaagcttca agccatattc      1140
acacttggat tgttagtggt gtataaactc ttgccctctg ataaggattc ttttcagcca      1200
gcgttattac aaggcataca gactattgac aacattgtcg aagggccaac tgattatgag      1260
gttttctcac aacctacatt tgattgggat acgtataatt catga                     1305
```

<210> SEQ ID NO 7
<211> LENGTH: 20
<212> TYPE: DNA
<213> ORGANISM: Artificial Sequence
<220> FEATURE:
<223> OTHER INFORMATION: guide RNA

<400> SEQUENCE: 7

```
acttcaatta cgacgtcgct                                                    20
```

<210> SEQ ID NO 8
<211> LENGTH: 20
<212> TYPE: DNA
<213> ORGANISM: Artificial Sequence
<220> FEATURE:
<223> OTHER INFORMATION: Guide RNA

<400> SEQUENCE: 8

```
cagagctgcc gccctcaata                                                    20
```

<210> SEQ ID NO 9
<211> LENGTH: 20
<212> TYPE: DNA
<213> ORGANISM: Artificial Sequence
<220> FEATURE:
<223> OTHER INFORMATION: Guide RNA

<400> SEQUENCE: 9

```
ataaggctgt ccaggacctc                                                    20
```

PLANTS RESISTANT TO INFECTION BY PEPINO MOSAIC VIRUS

CROSS-REFERENCE TO RELATED APPLICATIONS AND PRIORITY

This patent application claims priority from PCT Application No. PCT/EP2022/066499 filed Jun. 16, 2022, which claims priority from Spanish Patent Application No. P202130569 filed Jun. 18, 2021.

The present invention relates to plants comprising in their genome a gene that has been inactivated rendering the plant resistant to Pepino mosaic virus (PepMV) infection. The present invention also refers to the inactivation of the gene required for PepMV infection. The invention encompasses parts of these plants and their progeny that comprise said gene inactivation and, as a consequence, an improved phenotype in terms of PepMV infection resistance. Methods for obtaining plants, plant parts or seeds with resistance to PepMV infection are also part of this invention. The present invention further relates to the gene and sequences linked to it as markers for selecting plants resistant to PepMV infection. Therefore, the present invention belongs to the field of agriculture.

BACKGROUND ART

Viruses, in particular plant viruses, have small genomes that encode very small protein repertoires; with these few tools, viruses need to complete their cycles, including replication, trafficking within the host, counteracting host defenses and transmission among hosts, just to cite major functions. To achieve this, viruses kidnap and subvert the plant cell machinery, interacting with host factors that have proviral functions (Hyodo and Okuno, 2020, Advances in Virus Research, vol 107. Academic Press, Cambridge, pp 37-86); host proviral factors are often referred to as host susceptibility factors, because in their absence (or in the presence of an isoform non-functional for the virus), the host is not susceptible or is not fully susceptible. Attending to the phenotype of the plant-virus interaction, loss-of-susceptibility is equivalent to plant resistance (Kourelis and van der Hoorn, 2018, Plant Cell 30, 285-299), and therefore it has paramount interest in breeding. Plant breeders have used recessive resistance genes to build virus resistant cultivars along the years; in the cases studied with sufficient depth, all recessive virus-resistance genes conform to the hypothesis of encoding a proviral factor (Nicaise, 2014, Front Plant Sci 5, 1-18). Virus recessive resistance genes characterized to date within the natural diversity of crop species seem to belong to just one class, encoding eukaryotic translation initiation (eIF) factors of the 4E and 4G families (Truniger and Aranda, 2009, Advances in Virus Research, vol 75. Academic Press, Cambridge, pp 119-159). A different picture emerges when collections of mutants from model species are screened for loss-of-susceptibility to viruses; in this case, host factors different than eIF4E or 4G have been described (Makiinen, 2020, Ann Appl Biol 176, 122-129). However, their use in breeding virus resistant crop varieties is still a possibility poorly explored.

Pepino mosaic virus (PepMV) is a single stranded, positive sense RNA virus that belongs to the genus Potexvirus (family Alphaflexiviridae) and is epidemic in tomato crops worldwide; indeed, PepMV is causing very important economic losses in intensive tomato crops all over the world. The species Pepino mosaic virus is quite diverse, with at least five strains described to date. Given its economic impact, screenings to identify sources of resistance to PepMV have been performed in collections of Solanum spp. accessions (Soler et al., 2011, J. Plant Dis Prot 118, 149-155), but with limited success; identified resistances are partial and/or strain-specific which, together with the genetic distance of the resistance source to cultivated tomato, make them of limited interest in breeding. Host factors interacting with PepMV factors have also been identified; this is the case of heat shock cognate 70 (Hsc70) isoforms that interact with the PepMV coat protein (CP) (Mathioudakis et al., 2014, Mol Plant-Microbe Interact 27, 135.6-1369). Hsc70 seems to have a proviral function for PepMV, but its silencing induces a severe phenotype in the target plants (Mathioudakis et al., 2014, Mol Plant-Microbe Interact 27, 135.6-1369), making it unusable for breeding. A few other proviral factors have been identified for potexviruses, but their functions have not been tested for PepMV, or no use in breeding tomato PepMV-resistant varieties has been envisaged for them.

Therefore, new mechanisms that reduce the susceptibility of plants to PepMV infection are required, wherein such mechanisms work for several or all strains of PepMV, and are stable mechanisms which resist virus adaptation and evasion, to be useable in breeding.

DESCRIPTION OF THE INVENTION

In order to address the aforementioned lack of useable resistance to PepMV in plants, the authors screened a collection of tomato mutant plants to identify mutations that showed association with reduced susceptibility to PepMV. The screening resulted in the discovery of mutant plants with reduced viral loads and absence of the symptoms typical of PepMV infection. The genome of such mutants was characterized by bulked segregant analysis coupled to high throughput sequencing, to determine the source of the resistance of plants to PepMV infection. The source was finally determined to be the inactivation of a particular gene encoding a protein. Through back cross to the wild type plant and progenies analyses it could be established that the resistance has a recessive nature (see examples) as the segregating frequencies fit almost to perfection to the expected gene segregation in a model in which resistance is monogenic and recessive. The mutant plants have no obvious phenotype other than improved PepMV resistance or reduced susceptibility to PepMV (see examples).

Therefore, a first aspect of the present invention refers to a plant (from here onwards the plant of the invention) or part thereof, a reproductive or propagating plant material including seeds, (from here onwards the reproductive or propagating plant material of the invention), or a plant cell (from here onwards the plant cell of the invention) characterized in that it comprises a gene (from here onwards the gene of the invention) which encodes a protein, wherein said protein comprises an amino acid sequence with at least 60%, 62%, 65%, 70%, 75%, 80%, 85%, 90%, 91%, 92%, 93%, 94%, 95%, 96%, 97%, 98%, 99% or 100% sequence identity with SEQ ID NO: 1 and said gene has been inactivated. In a preferred embodiment, the plant of the invention or part thereof, the reproductive or propagating plant material of the invention or the plant cell of the invention is not exclusively obtained by means of an essentially biological process.

As stated, the inventors have determined mutant plants with resistance to the infection by PepMV. The term "plant" as used herein includes whole plants, any "reproductive or propagating material" for a plant, progeny of the plants and parts of plants, including seeds, siliques, fruits, leaves, flowers, shoots, stems, tubers, roots, isolated plant cells, callus, tissues and organs. References to a plant may also include plant cells, plant protoplasts, plant tissue cultures, plant calluses, plant clusters and plant cells which are intact in plants or parts of plants, such as embryos, pollen, ovules, seeds, leaves, flowers, branches, fruits, grains, spikes, ears, hulls, stems, roots, root tips and the like. The offspring, variants and mutants of any of the plants described herein are within the scope of the present invention. The seeds of any of said plants are also included. As it is used herein, the term "parts of a plant" includes any part or parts of a plant including the seeds, siliques, fruits, leaves, flowers, shoots, stems and/or roots.

As the expert in the field is aware and knowledgeable about, the present invention may also be performed in plant cells. The term "plant cell" as used herein includes plant cells derived and/or isolated from plant cell tissue or from plant cell culture.

The invention herein described relates to plants with improved resistance to infection by PepMV or improved phenotype in terms of PepMV infection resistance. In another preferred embodiment the plant of the invention or part thereof, or the reproductive or propagating plant material of the invention, or the plant cell of the invention is characterized by having improved resistance or reduced susceptibility to PepMV infection or improved phenotype in terms of PepMV infection resistance compared to wild-type control plants.

As used herein the expressions "resistance to PepMV infection" and "reduced susceptibility to PepMV infection" refers to a reduction of the viral titer or the absence of the virus in the plant of the invention, or the reproductive or propagating plant material of the invention, or the plant cell of the invention in comparison to wild-type control plants, materials or plant cells. In a preferred embodiment the reduction of the viral titer is of at least 50%, 60%, 65%, 70%, 75%, 80%, 85%, 90%, 95% or 100% in comparison to a wild-type plant. In addition, the expressions "resistance to PepMV infection" and "improved phenotype in terms of PepMV infection resistance" refer to a reduction or the absence of the symptoms provoked by the infection. In a preferred embodiment the resistance to PepMV infection or improved phenotype in terms of PepMV infection resistance leads to reduction of the symptoms according to the disease scale test (see examples) to better score in such a test than wild type plants, that is in a 0-2 scale (were 0 is absence of symptoms, 1 is sporadic bright yellow spots in newly emerging leaves, and 2 is bright yellow mosaic affecting all newly emerged leaves) from 2 to 1 or to 0 score.

The inventors of the present invention determined that the resistance to PepMV infection or improved phenotype in terms of PepMV infection resistance is due to the inactivation of the gene of the invention. In a preferred embodiment the plant of the invention or part thereof, or the reproductive or propagating plant material of the invention, or the plant cell of the invention is characterized in that the inactivated gene encodes for a protein wherein said protein comprises an amino acid sequence with has at least 60%, 62%, 65%, 70%, 75%, 80%, 85%, 90%, 91%, 92%, 93%, 94%, 95%, 96%, 97%, 98%, 99%, or 100% identity with SEQ ID NO: 1. In another preferred embodiment the plant of the invention, or the reproductive or propagating plant material of the invention, or the plant cell of the invention is characterized in that the inactivated gene encodes for a protein, wherein said protein amino acid sequence consists of SEQ ID NO: 1.

```
                                          SEQ ID NO: 1
MIQSSFSADSPSMAANSTESPPPAAGDGDENYDVAWYGNIQYLLNISAIG

ALTCLLIFIFGKLRSDHRRMPGPTAIVSKLLAAWHATGVEIARHCGADAA

QYLLIEGGSSALLLFLALLSLAVMLPLNIYAGKAPMADQFSKTTINHIEK

GSPLLWIHFIFVVIVVVLVHYGISEIQERLKITRLRDGYGNPSNSGTNVS

AIFSIMVQGVPKTLGEDKTPLVEYFQHKYPGKVYRVVVPMDLCALDDLAT

ELVKVREDISKLVSRIELRGYLNEGEEDEYNNDSVNGRGLLERLCELWRK

AKDTWYHVVDQLGESDEERLRKLQELRADLEMEMASYKEGRARGAGVAFV

VEKDVFTANKAVQDLRNEKRRRYGRFFSVIELQLQRNOWKVERAPLATDI

YWNHLGSTKESLKLRRVLVNTCLLLMLLFCSSPLAVISAIQSAGRIINAE

AMDHAQMWLNWVQGSSWLATIIFQFLPNVLIFVSMYIVVPSVLSYLSKFE

QHLTVSGEQRAELLKMVCFFLVNLILLRALVESTLEGALLSMGRCYLDGE

DCKKIEQYMTASFLTRTCLSSLAFLITSSELGISEDLLAPIPWIKKKLQK

FRKNDMLQLVPERSEEYPLENQDIDSLERPLIHERSSTVIADNNGELHDA

SPNEIDEPGQDLSEYPPVSRTSPVPKPKFDFAQYYAFNLTIFALTLIYCS

FAPLVVPVGAVYFGYRYLVDKYNFLFVYRVRGFPAGNDGRLMDTVLSIMR

FCVDLFLLSMLLFFSVRGDSTKLQAIFTLGLLVVYKLLPSDKDSFQPALL

QGIQTIDNIVEGPTDYEVFSQPTFDWDTYNS
```

The term "inactivated" as used herein refers to decreasing, reducing, or totally or partially inhibiting the expression of the target gene or target allele by at least about 50%, 60%, 65%, 70%, 75%, 80%, 85% to 100% compared to its normal expression in a wild-type plant. In addition, the term "inactivation" is also used herein as a synonym of "silenced" and as a synonym of "knockout" which refers to the modification of the gene nucleotide sequence in a way as to produce a non-functional messenger RNA or a reduced function or non-functional protein. In a more preferred embodiment the plant of the invention, or the reproductive or propagating plant material of the invention, or the plant cell of the invention is characterized in that the inactivated gene encodes for a protein wherein said protein comprises SEQ ID NO: 2, preferably consists of SEQ ID NO: 2. SEQ ID NO: 2 results from a mutation in SEQ ID NO: 1 at position 554 wherein the amino acid lysine has been replaced by stop codon. In another preferred embodiment, the plant of the invention, or the reproductive or propagating plant material of the invention, or the plant cell of the invention is characterized in that the inactivated gene encodes for a protein wherein said protein comprises SEQ ID NO: 3, preferably consists of SEQ ID NO: 3. SEQ ID NO: 3 results from the deletion of amino acids 11 through 408 of SEQ ID NO: 1.

```
                                          SEQ ID NO: 2
MIQSSFSADSPSMAANSTESPPPAAGDGDFNYDVAWYGNIQYLLNISAIG

ALTCLLIFIFGKLRSDHRRMPGPTAIVSKLLAAWHATGVEIARHCGADAA

QYLLIEGGSSALLLFLALLSLAVMLPLNIYAGKAPMADQFSKTTINHIEK

GSPLLWIHFIFVVIVVVLVHYGISEIQERLKITRLRDGYGNPSNSGTNVS

AIFSIMVQGVPKTLGFDKTPLVEYFQHKYPGKVYRVVVPMDLCALDDLAT

ELVKVREDISKLVSRIELRGYLNEGEEDEYNNDSVNGRGLLERLCFLWRK
```

5

-continued

```
AKDTWYHVVDQLGESDEERLRKLQELRADLEMEMASYKEGRARGAGVAFV

VFKDVFTANKAVQDLRNEKRRRYGREFSVIELQLQRNQWKVERAPLATDI

YWNHLGSTKESLKLRRVLVNTCLLLMLLFCSSPLAVISAIQSAGRIINAE

AMDHAQMWLNWVQGSSWLATIIFQFLPNVLIFVSMYIVVPSVLSYLSKFE

QHLTVSGEQRAELLKMVCFFLVNLILLRALVESTLEGALLSMGRCYLDGE

DCK
```

```
                                        SEQ ID NO: 3
MIQSSFSADSQKFSLKLRRVLVNTCLLLMLLFCSSPLAVISAIQSAGRII

NAEAMDHAQMWLNWVQGSSWLATIIFQFLPNVLIFVSMYIVVPSVLSYLS

KFEQHLTVSGEQRAELLKMVCFFLVNLILLRALVESTLEGALLSMGRCYL

DGEDCKKIEQYMTASELTRTCLSSLAFLITSSELGISFDLLAPIPWIKKK

LQKFRKNDMLQLVPERSEEYPLENQDIDSLERPLIHERSSTVIADNNGFL

HDASPNEIDFPGQDLSEYPPVSRTSPVPKPKEDFAQYYAENLTIFALTLI

YCSFAPLVVPVGAVYFGYRYLVDKYNFLFVYRVRGFPAGNDGRLMDTVLS

IMRFCVDLFLLSMLLFFSVRGDSTKLQAIFTLGLLVVYKLLPSDKDSFQP

ALLQGIQTIDNIVEGPTDYEVFSQPTEDWDTYNS
```

In the present invention the inactivation refers to the gene of the invention. As used in the present description the term "gene" refers to any segment of DNA associated with a biological function. Therefore, the genes include encoding sequences and/or the regulating sequences required for their expression. The genes also include unexpressed DNA segments which, for example, form recognition sequences for other proteins. The genes can be obtained from a variety of sources, including cloning from a source of interest or synthesis from known or predicted sequence information, and may include sequences designed to have the desired parameters. The expression "encodes for a protein" as used herein refers to the fact that the gene of the invention comprises the necessary nucleotide sequences that allow it to be transcribed into a messenger RNA which is thereafter translated into an amino acid sequence which will be folded into a functional protein. In a preferred embodiment the gene of the invention comprises the genomic DNA sequence SEQ ID NO: 4. In another preferred embodiment the gene of the invention is inactivated and comprises a nucleotide sequence according to SEQ ID NO: 5 or SEQ ID NO: 6. In another preferred embodiment the gene of the invention is inactivated and consists of the nucleotide sequence SEQ ID NO: 5 or SEQ ID NO: 6.

As aforementioned, a plant with resistance to infection by PepMV or improved phenotype in terms of PepMV infection resistance refers to a plant with lower viral titer or reduced infection symptoms in comparison with a wild-type plant. Likewise, the inactivation of the gene of the invention also comprises a reduction of the level of expression of the gene, a reduction of the level of available mRNAs transcribed from said gene, a reduction of the amount of functional protein encoded by said gene, as well as the complete abrogation of the gene and/or of the functional protein. In the cases when there is a reduction, said reduction is determined in comparison to a wild-type plant. The term "wild-type" (also written "wildtype", "wild type" or WT), as used herein, refers to a typical form of a plant or a gene as control plant not comprising the inactivated gene of the invention, the better version of the control plant being near isogenic lines. A "wild type plant" refers to a plant with the phenotype corresponding to a plant not comprising the inactivated gene of the invention in the natural population.

Despite having been identified as the source of the reduced susceptibility to PepMV infection in tomato plants or of the improved phenotype in terms of PepMV infection resistance, the gene of the invention and the encoded protein thereof have orthologs with similar structural protein characteristics, as showed by the inventors (see examples). In order to identify the protein homologs, experts in the art commonly use the identity of the amino acid sequence between two proteins. The term "identity" as used herein refers to the proportion of identical amino acids or nucleotides between two compared peptides/proteins or nucleotide sequences, respectively, along their full-length sequence. The methods for comparing sequences are known in the state of the art, and include, but not limited to, the programs BLASTP or BLASTN, EMBOSS Needle, ClustalW and FASTA. We can consider that peptides, proteins or nucleotide sequences with percent identities of at least 60%, 70%, 80%, 90% will maintain the same properties as the sequence to which they are being compared to.

The identification of homologs of the gene of the invention indicates that the inactivation of said homologs can be used to create resistant plants to PepMV infection or with improved phenotype in terms of PepMV infection resistance. Therefore, in another preferred embodiment the plant of the invention or part thereof, or the reproductive or propagating plant material of the invention, or the plant cell of the invention belongs to the Solanaceae family. In another preferred embodiment the plant of the invention or part thereof, or the reproductive or propagating plant material of the invention, or the plant cell of the invention belongs to the *Solanum* sp, the *Capsicum* sp, *Nicotiana* sp or *Physalis* sp genera. In a yet more preferred embodiment, the species are selected from the list consisting of: *S. lycopersicum, S. tuberosum, S. melongena, S. pennellii. S. pimpinellifolium, S. peruvianum, S. cheesmanii, S. galapagense, S. chilense, S. aethiopicum, S. quitoense, S. torvum, S. muricatum, S. betaceum, S. chmielewskii, S. arcanum, S. cornelliomulleri, S. habrochaiti, S. huaylasense, S. neorickii, S. dulcamara, S. lycopersicoides, S. sitiens, S. juglandifolium, S. ochranthum* and *S. cheesmaniae.* The present invention also refers to the synonymous of these species, such as *Lycopersicon esculentum, Lycopersicon esculentum* Mill., *Lycopersicon esculentum* var. *esculentum, Solanum esculentum, Solanum esculentum* Dunal.

It is to be understood that a species also includes all subspecies and varieties or cultivars therein. The term "variety" as used herein refers to a group of plants within a species that share characters that separate them from other possible varieties within that species. Such distinctive trait or set of traits must be stable after reproduction and sufficiently homogeneous among its individuals and progeny. For autogamous or self-pollinating species, as in the Solanaceae family, most commercial varieties are pure lines or inbreds, and F1 hybrids between two inbreds. The term "cultivar" as used herein refers to a plant having a biological status other than a "wild" status, which "wild" status indicates the original non-cultivated, or natural state of a plant or accession. The term "cultivar" includes, but is not limited to, semi-natural, semi-wild, weedy, traditional and heirloom cultivars, landrace, breeding material, research material, breeder's line, synthetic population, hybrid, founder stock/base population, inbred line (parent of hybrid cultivar), segregating population, mutant/genetic stock, and advanced/improved cultivar.

Therefore, in another preferred embodiment of the plant of the invention or part thereof, or the reproductive or propagating plant material of the invention, or the plant cell of the invention, the species *S. lycopersicum* comprises the varieties/cultivars Anna Russian, Applause, Aussie, Baladre, Bella Rosa, Black cherry, Black Pear, Black russian, Blondkopfchen, Brandywine, Cabri, Caracas, Carbón, Ceylan, Cherokee purple, Cherry, Comanche, Costoluto genovese, Ditmarcher, Dombito, Estrella, Eros, Gallician, Glacier, Gartenperle, Green sausage, Grushovka, Harzfeuer, Hugh, Jersey devil, Juboline, Kosovo, Krim black, Kumato, Liguria, Limachino, Lime green salad, Manitoba, Marvel stripe, Moneymaker, Marglobe, Meltine, Monserrat, Muchamiel, Nemato, Opalka, Pera de Girona, Piña Hawaiana, Rio grande, RAF, Roma, Siberian, Sprite, Sugary, Sun sugar, Sobeto, Sonatine, Tigerella, Terrades, Vergel, White Queen, Raf Claudia, Roma, Valenciano, Adoration, Alicante, Azoychka, Better Boy, Big Beef, Big Rainbow, Blaby Special, Black Krim, Branywine, Campari, Celebrity, Canario (tomato), Tomkin, Early Girl, Enchantment, Ferris Wheel, Flamenco, Fourth of July, Garden Peach, Gardener's Delight, Granadero, Great White, Green Zebra, Hanover tomato, Japanese Black Trifele, Jubilee, Juliet, Lillian's Yellow, Matt's Wild Cherry, Micro-Tom, Moneymaker, Monterosa, Mortgage Lifter, Mr. Stripey, Pantano Romanesco, Plum tomato, Raf tomato, Rebellion, Red Currant, Rosa de Barbastro, San Marzano, San Pedro, Sasha Altai, Tiny Tim, Cherry Bambelo, Cherry Nebula, Santorini, Tomaccio, Yellow Pear, White Queen, Corazón de Buey, Angela, Colgar en Rama, Ciruela Negro, Optima, Pata Negra, Copia, Velasco, Montenegro, Vertyco, Ventero, Ramyle, Pitenza, Paladium, Mayoral, Razymo, Motto, Caniles, Byelsa, Royalty, Trujillo, Delizia, Dumas Duratom, Larguero, Torry, Tovistar, Pintón, Grueso, Larga Vida, Marenza, Window box Roma, Ninette, Retinto, Boludo, Anairis, Tobi Star, Myla, Guarapo, Atago, Jawara, Velasco, Manitu, Colbi, Duraton, Patriarca, Danubio, Intense, Pera Fitto, Vernal, Cecilio, Cherry Kumato, Cherry Amarillo, Cherry Redondo, Cherry Ministar, Cherry Guindos, Cherry Marinica and Cherry Angel.

In another preferred embodiment of the plant of the invention or part thereof, or the reproductive or propagating plant material of the invention, or the plant cell of the invention, the species *S. tuberosum* comprises the varieties/cultivars Kennebec, Monalisa, Desirée, Bintje, Álava, Palogan, Pedro Muñoz, Roja Riñón, Duquesa, Goya, Olalla, Turia, Victor, Lora, Gauna, Alda, Belda, Buesa, Iturrieta, Diba, Fénix, Onda, Arene, Asun, Ayala, Edurne, Gorbea, Idoia, Iker, Inca, Isla, Mayka, Mikel, Montico, Nagore, Nerea, Zadorra, Zarina and Zela.

In order to obtain the plant of the invention, the reproductive or propagating plant material, or the plant cell of the invention as referred to herein, both exclusively biological methods and other than exclusively biological methods or procedures were used. As such, the expression "not exclusively obtained by means of an essentially biological process" refers to a host organism such as a plant cell, a seed, a plant or part of a plant whose genome or proteome has been modified by methods other than essentially biological methods such as crossing, inter-breeding, selective breeding, introgression, selfing or other biological processes which do not involve a technical step which modifies the genome or proteome. Examples of methods, other than essentially biological processes, to obtain a plant wherein the gene of the invention is inactivated are, without limitation, somatic hybridization, mutagenesis with mutagenic agents like, but not limited to, ionizing radiation such as with x-rays, fast neutrons, UV radiation etc. or chemical agents such as, but not limited to, ethyl methanesulfonate (EMS), diethyl sulfate (des) ethyleneimine (ei), propane sultone, N-methyl-N-nitrosourethane (mnu), N-nitroso-N-methylurea (NMU), N-ethyl-N-nitrosourea (enu), sodium azide and genetic engineering. Examples of the latter methods, are, without limitation, the insertion of exogenous nucleic acids into the genome of the target plant using microbial vectors, microprojectile bombardment, electroporation, microinjection, transposons, or the transformation of the endogenous nucleic acids or genome editing techniques including CRISPR/Cas techniques or others such as, without limitation, those based in the used of Zinc finger nuclease (ZFN), Transcription activator—like effector nucleases (TALENs), etc.

For purposes of the present invention, the expression "not exclusively obtained by means of an essentially biological process" refers to plants whose genetic material has been deliberately modified as to alter the gene which encodes a protein wherein said protein comprises an amino acid sequence with at least 60%, 62%, 65%, 70%, 75%, 80%, 85%, 90%, 91%, 92%, 93%, 94%, 95%, 96%, 97%, 98%, 99%, or 100% sequence identity to the SEQ ID NO: 1, or wherein said protein amino acid sequence consists of SEQ ID NO: 1. Preferably, said protein is the hyperosmolality-gated calcium permeable channel 4.1 (OSCA4.1). Specifically, the plants of the invention have been modified by both essentially and non-essentially biological process to inactivate the expression of the gene of the invention described herein and/or to modify its expression product in order for said product to be functionally reduced or non-functional.

The plant of the invention, as all other plants, is composed of cells, tissues and organs, which fall within the scope of the invention. Thus, in another preferred embodiment the reproductive or propagating material is selected from a cell, a fruit, a seed, a tuber or a progeny. In yet another preferred embodiment of the plant of the invention, the part of the plant is selected from a list consisting of: a leaf, a stem, a flower, an ovary, or a callus. These components of the plant of the invention both the reproductive or propagating material and the part of the plant of the invention are also characterized in that they comprise a gene which encodes for a protein, wherein said protein comprises an amino acid sequence with at least 60%, 62%, 65%, 70%, 75%, 80%, 85%, 90%, 91%, 92%, 93%, 94%, 95%, 96%, 97%, 98%, 99%, or 100% sequence identity with SEQ ID NO: 1 and said gene has been inactivated.

In order to obtain the plant of the invention, the reproductive or propagating plant material of the invention, the plant cell of the invention, or any of the components of the plant of the invention, several methods are available to the expert of the art, being that the expert will know the best practice to apply the chosen method as to obtain a plant with the gene of the invention inactivated. Hence, another aspect of the present invention relates to a method for producing the plant of the invention, or the reproductive or propagating plant material of the invention, or the plant cell of the invention, or the components of the plant of the invention, wherein said plant or part thereof, reproductive or propagating plant material, or plant cell shows resistance to infection by PepMV or improved phenotype in terms of PepMV infection resistance, said method (from here onwards the method of the invention) comprising:

a) subjecting the plant or part thereof, the reproductive or propagating plant material, or the plant cell to mutagenesis either random or directed, and b) detecting a mutation in a gene which encodes a protein, wherein said protein comprises an amino acid sequence with at least 60%, 62%, 65%, 70%, 75%, 80%, 85%, 90%, 91%, 92%, 93%, 94%, 95%, 96%, 97%, 98%, 99%, or 100% sequence identity with SEQ ID NO: 1, in the plant or part thereof, the reproductive or propagating plant material, or the plant cell, and wherein said mutation leads to an inactivation of the gene.

In a preferred embodiment of the method of the invention the plant, or the reproductive or propagating plant material of the invention, or the plant cell of the invention, or the components of the plant of the invention belong to the Solanaceae family. In a yet another preferred embodiment of the method of the invention the plant, or the reproductive or propagating plant material of the invention, or the plant cell of the invention, or the components of the plant of the invention belong to the *Solanum* sp., *Capsicum* sp., *Nicotiana* sp. or *Physalis* sp genera. In a more preferred embodiment of the method of the invention the plant, or the reproductive or propagating material of the invention, or the plant cell of the invention, or components of the plant of the invention belong to a species selected from the list consisting of: *Solanum lycopersicum, S. tuberosum, S. pennellii, S. pimpinellifolium, S. peruvianum, S. cheesmanii, S. galapagense, S. chilense, S. melongena, S. aethiopicum, S. quitoense, S. torvum, S. muricatum, S. betaceum. S. chmielewskii, S. arcanum, S, cornelliomulleri, S. habrochaiti, S. huaylasense, S. neorickii, S. dulcamara, S. lycopersicoides, S. sitiens, S. juglandifolium, S. ochranthum,* and *S. cheesmaniae.* It is to be understood that a species includes all subspecies and varieties or cultivars therein. Examples of varieties/cultivars for several species, without limitation, are listed earlier in the description and such varieties/cultivars are valid for the current aspect and its embodiments.

Methods to obtain plants, reproductive or propagating material, plant cells, progenies or part of plants, specifically wherein genes are inactivated, are widely known in the art and an expert would be able to discern the best method to apply to obtain the desired plant. Such methods include both directed and random mutagenesis strategies. Random mutagenesis strategies are mostly based, but not limited to, on techniques which induce mutations in the DNA of the cells, such as contact with a mutagenic agent, such as a chemical substance (such as ethylmethylsulfonate (EMS), ethylnitrosourea (ENU), etc.) or ionizing radiation (neutrons, such as in fast neutron mutagenesis, etc.), alpha rays, gamma rays (such as that supplied by a Cobalt 60 source), X-rays, UV-radiation, etc., or any combination thereof. Directed mutagenesis strategies include, but are not limited to, homologous recombination-dependent gene targeting, antisense RNA, directed transposon insertion, virus induced gene silencing and genome editing techniques including but not limited to CRISPR/Cas techniques.

As such, in a preferred embodiment of the method of the invention the gene of the invention is inactivated by mutagenesis with mutagenic agents, mutagenesis with chemical agents, genetic engineering or genome editing techniques, including CRISPR/Cas techniques.

The plant of the invention finds agricultural uses. Amongst said uses, the most widely use is the growth of the plant to obtain or generate feeding or consumable products. As such, another aspect of the present invention relates to a use of the plant of the invention, the reproductive or propagating plant material of the invention, the plant cell of the invention, or the components of the plant of the invention for producing an agro-industrial product, preferably wherein the agro-industrial product is a food or a feed.

Said use is closely related to a method for the production of the said agro-industrial product. Therefore, another aspect of the present invention relates to an agro-industrial product production method, preferably wherein the agro-industrial product is a food or a feed, comprising:

a) culturing the plant of the invention, the reproductive or propagating plant material of the invention, the plant cell of the invention, or the components of the plant of the invention, b) harvesting the fruit, the seeds, the tubers or the edible part of the plant to produce the agro-industrial product, and c) optionally, preparing the agro-industrial product for consumption either fresh or transformed.

The invention set forth in the present description and undermentioned claims relates to plants wherein the inactivation of the gene of the invention confers resistance to the infection by PepMV or with improved phenotype in terms of PepMV infection resistance. The present description also sets forth that plants with resistance to infection by PepMV or with said improved phenotype can be identified by screening for alterations in the nucleotide sequence of the gene of the invention which can affect the level of expression of said gene or screening for alterations in the level of the expression of the products of said gene. Therefore, another aspect of the present invention relates to the use of a gene as a biomarker, from here onwards the biomarker use of the invention, to select plants with resistance to infection by PepMV or with improved phenotype in terms of PepMV infection resistance, wherein said gene encodes for a protein which comprises an amino acid sequence with at least 60%, 62%, 65%, 70%, 75%, 80%, 85%, 90%, 91%, 92%, 93%, 94%, 95%, 96%, 97%, 98%, 99%, or 100% sequence identity with SEQ ID NO: 1. In another preferred embodiment of the biomarker of the invention the gene comprises a nucleotide sequence with at least 60%, 62%, 65%, 70%, 75%, 80%, 85%, 90%, 91%, 92%, 93%, 94%, 95%, 96%, 97%, 98%, 99%, or 100% sequence identity with SEQ ID NO: 4. If the gene being detected is altered in a way that warrants its inactivation, then the plant presents resistance to PepMV infection. Therefore, in another embodiment of the biomarker use of the invention, the biomarker is inactivated. In another preferred embodiment of the biomarker use of the invention, the biomarker is inactivated and it encodes for a protein that comprises an amino acid sequence according to SEQ ID NO: 2 or SEQ ID NO: 3. In yet another preferred embodiment of the biomarker use of the invention, the biomarker is inactivated and comprises a nucleotide sequence according to SEQ ID NO: 5 or SEQ ID NO: 6. The use of the biomarker of the present invention in a maker assisted breeding program to selected inbred lines, progeny and/or plants with the PepMV resistance trait is also part of the present description.

As used herein the term "biomarker" comprises any measurable substance in a plant whose presence is indicative of a biological state or a condition of interest. In the present invention, the biomarker relates to the nucleotide sequence of the gene of the invention, the products of the expression of the said gene or nucleotide sequences linked to it. Therefore, in a preferred embodiment of the biomarker use of invention, the selection is made by determining the nucleotide sequence of the gene or fragments of said nucleotide sequence and identifying alterations in it. In another embodiment the selection is made by detecting or quantifying the product of expression of the gene of the invention, wherein said products are selected from the list consisting of: complementary DNA or a fragment thereof, messenger RNA or a fragment thereof, and protein or a fragment thereof. In another preferred embodiment of the biomarker of the invention, the selection is made by further determining a marker locus which co-segregates with SEQ ID NO: 4, preferably wherein said marker locus is localized in a range of 100000 nucleotides upstream or downstream of the biomarker of the invention.

Another aspect of the present invention relates to a marker locus to select plants with resistance to infection by PepMV or with improved phenotype in terms of PepMV infection resistance, wherein said marker locus co-segregates with SEQ ID NO: 4 and is localized in a range of 100000 nucleotides upstream or downstream of SEQ ID NO: 4.

The term "marker locus" as used herein refers to specific, fixed position on a chromosome where a particular gene or genetic marker is located, which co-segregates with SEQ ID NO: 4. The term "co-segregates" as used herein refers to two or more genetic markers in one chromosome which are transmitted together as result of being in close physical proximity to one another, i.e., are linked. The marker locus can comprise or consist of any genetic nucleotide sequence or common trait, such as, without limitation, genes, introns, exons, enhancers, promoters, single nucleotide polymorphisms, small-scale insertions/deletions, transposable elements, microsatellites, or simply nucleotide fragments of 10, 20, 30, 40, 50, 60, 70, 80, 90, 100 or more base pairs of the nucleotide sequence.

The terms "upstream" and "downstream" as used herein relate to positions which are in the 5' direction or the 3' direction of the biomarker of the invention, respectively.

Methods to detect a biomarker are common knowledge of the field of the expert. For example, without limitation, the identification of alterations in the nucleotide sequence of the gene of the invention or fragments thereof can be performed by electrophoresis analysis or sequencing analysis of the products of a polymerase chain reaction (PCR) of the whole gene or a fragment thereof. Said "alterations in the nucleotide sequence" as used herein refers to mutations in the nucleotide sequence, be it nucleotide substitutions, insertions or deletions, which when present in the protein coding region of the gene of the invention can result in missense mutations, where an amino acid is replaced by another one, or nonsense mutations where an early stop codon is formed. Said types of alterations are more likely to lead to functionally reduced or non-functional expression products of the gene of the invention, and as such an inactivation of the gene or stronger silencing of the gene of the invention. The expression "alterations in the nucleotide sequence" as used herein also encompasses alterations which occur in the gene of the invention outside the protein coding region, such as, without limitation, the promoter and/or enhancer region, or in sequences linked to the gene of the invention, such as, and without limitation, enhancers, which can affect the level of expression of the products of the gene of the invention.

The alterations in the nucleotide sequence of the biomarker can, as the expert in the art is aware, be detected in a small fragment, or fragments, of the entire sequence, if said fragment can be clearly identified and mapped to the native or wild-type sequence in order to identify said alterations and be able to determine their potential in inactivating the biomarker. Said fragment can range from 10 base pairs up to the full length of the biomarker. Therefore, in a preferred embodiment the biomarker comprises a fragment of at least 10, 20, 30, 40, 50, 60, 70, 80, 90 or 100 base pairs of the gene sequence.

The detection of the expression products of the gene of the invention can be done by detecting or quantifying the level of messenger RNA (mRNA) derived from the transcription of the gene, or a fragment thereof, wherein the analysis of the mRNA level can be performed, for example, and without limitation, by polymerase chain reaction (PCR) amplification, reverse transcription PCR (RT-PCR), reverse transcription in combination with ligase chain reaction (RT-LCR), or any other nucleic acid amplification method; DNA microarrays produced using oligonucleotides deposited by any mechanism; DNA microarrays made from oligonucleotides synthesized in situ by photolithography or by any other mechanism; in situ hybridization using specific probes labelled by any labelling method; by electrophoresis gels; by membrane transfer and hybridization with a specific probe; by nuclear magnetic resonance or any other imaging technique using paramagnetic nanoparticles or any other type of detectable nanoparticles functionalized with DNA/RNA probes, antibodies or by any other means.

The term "mRNA fragment" as used herein refers to nucleotide sequence obtained by transcription of the gene of the invention, wherein said sequence is missing one or more nucleotides from the 5 prime and/or 3 prime regions or any region thereof in comparison to the full nucleotide sequence obtained from the transcription of the gene of the invention.

In addition to detecting mRNA, the detection of the biomarker of the invention can also be made by detecting and/or quantifying the protein product of the biomarker, or a fragment thereof, of the invention. As previously, said methods are well known in the art and include, without limitation, Western blot, protein array, ELISA, immunohistochemistry o immunoprecipitation.

The terms "protein fragment" as used herein refers to a protein which is missing one or more amino acids from the N-terminus and/or C-terminus or any part of the protein in comparison to the normal full-length protein, wherein said fragment does not retain the original function of the full-length protein. In the present invention, the protein is the OSCA4.1 protein obtained by the translation of the gene of the invention.

One of the more common ways to detect proteins or protein fragments is with the use of antibodies and techniques that use said antibodies. The term "antibodies" as used herein refers to immunoglobulin molecules and immunoactive fragments of immunoglobulin molecules, i.e., molecules which contain a binding site of an antigen which binds specifically (immunoreacts) with a protein. There are five main classes of immunoglobulins: immunoglobulin M (IgM), immunoglobulin D (IgD), immunoglobulin G (IgG), immunoglobulin A (IgA) and immunoglobulin E (IgE).

Relating to the use herein described, another aspect of the present invention relates to a method for selecting plants with resistance to infection by PepMV or with improved phenotype in terms of PepMV infection resistance compared to the wt, from here onwards the method of selection of the invention, comprising the steps of:

a) Detecting a gene which encodes for a protein wherein said protein comprises an amino acid sequence with at least 60%, 62%, 65%, 70%, 75%, 80%, 85%, 90%, 91%, 92%, 93%, 94%, 95%, 96%, 97%, 98%, 99%, or 100% sequence identity with SEQ ID NO: 1, and b) Determining if said gene of step a) is inactivated, wherein an inactivated gene is indicative of resistance to infection by PepMV or improved phenotype in terms of PepMV infection resistance compared to the wt.

In a preferred embodiment of the method of selection of the invention the detection in step (a) is made by determining the nucleotide sequence of the gene or a fragment thereof. In another preferred embodiment of the method of selection of the invention, the detection in step (a) is made by detecting or quantifying the product of expression of the gene of the invention, wherein said products are selected from the list consisting of: complementary DNA or a fragment thereof, messenger RNA or a fragment thereof, and protein or a fragment thereof.

The terms and expressions "plants", "resistance to infection by PepMV", "gene", "protein", "amino acid sequences", "identity", "inactivated", "silenced", "fragment of a gene", "fragment of a protein", "messenger RNA", "fragment of mRNA", "complementary DNA", fragment of cDNA" have been defined previously in relation to previous aspects of the present invention and said definitions are equally valid for the present aspect and its embodiments.

Methods for detecting a gene, either by determining its nucleotide sequence or a fragment thereof, or its expressions products like mRNA; cDNA or protein or fragments thereof have previously been described in relation to the biomarker use of the invention regarding methods and techniques of detecting alterations in the nucleotide sequence of the biomarker or detecting alterations in the expression products of the biomarker. Said methods and techniques are equally valid for the present aspect and its embodiments.

Other uses and methods to generate the plant of the invention or part thereof, the reproductive or propagating plant material of the invention, or the plant cell of the invention are methods which rely on substantial human intervention in biological processes making use of the biomarker of the invention as to obtain the desired outcome. Therefore, another aspect of the present description is the use of the biomarker of the invention in an assisted breeding program to selected plants with resistance to infection by PepMV or with improved phenotype in terms of PepMV infection resistance compared to the wild type. Yet another aspect of the present invention relates to a use of the biomarker of the invention for the screening a population of plants for the presence of an inactivated allele of the gene of the invention, wherein said presence is indicative of an increased resistance to infection by PepMV or improved phenotype in terms of PepMV infection resistance compared to the wild type.

The term "assisted breeding program", also known as "marker aided selection", as used herein refers to the selection process wherein a trait of interest is selected based on a marker which is linked to said trait, rather than the trait itself. In the present invention the marker is the biomarker of the invention and the trait is the resistance to infection by PepMV or the improve phenotype in terms of PepMV infection resistance.

Another aspect of the present invention relates to a method for producing a hybrid of the plant of the invention or part thereof, a hybrid of the reproductive or propagating plant material of the invention, or a hybrid of the plant cell of the invention, wherein said hybrid plant or part thereof, hybrid reproductive or propagating plant material, or hybrid plant cell shows resistance to infection by PepMV or improved phenotype in terms of PepMV infection resistance, from here onwards the hybrid method of the invention, comprising:

a) Crossing the plant of the invention or part thereof, the reproductive or propagating plant material of the invention, or the plant cell of the invention with a second plant; and
    b) Harvesting the hybrid progeny of said crossing.

As used herein the terms "hybrid", "hybrid plant," or "hybrid progeny" refer to an individual produced from genetically different parents (e.g., a genetically heterozygous or mostly heterozygous individual). In a preferred embodiment of the hybrid method of the invention the second plant in step a) belongs to *Solanum* sp., or *Capsicum* sp., *Nicotiana* sp. or *Physalis* sp. In another preferred embodiment the second plant is selected from a list consisting of: *Solanum lycopersicum, S. tuberosum, S. pennellii, S. pimpinellifolium, S. peruvianum, S. cheesmanii, S. galapagense, S. chilense, S. melongena, S. aethiopicum, S. quitoense, S. torvum, S. muricatum, S. betaceum, S. chmielewskii, S. arcanum, S. cornelliomulleri, S. habrochaiti, S. huaylasense, S. neorickii, S. dulcamara, S. lycopersicoides, S. sitiens, S. juglandifolium, S. ochranthum,* and *S. cheesmania.*

In another embodiment of the hybrid method of the invention the second plant of step a) is an inbred line and the hybrid progeny of step b) is a single-cross F1 hybrid. The term "inbred line" as used herein refers to a genetically homozygous or nearly homozygous population. An inbred line can, for example, be derived through several cycles of brother/sister breeding, selfing or in a dihaploid production. As used herein, the expression "single-cross F1 hybrid" refers to a first generation (or "Filial 1") hybrid produced from a cross between two inbred lines. In some preferred embodiments of the hybrid method of the invention, inbred lines breed true for one or more phenotypic traits of interest. In another further preferred embodiment of the hybrid method of the invention the inbred line is an elite line. As used herein the term "elite line" refers to plant lines which provide constant quality product. Elite lines are the result of many years of inbreeding and combine multiple superior characteristics such as high yield, fruit quality, and resistance to pests, disease, or abiotic stress. The average yield of these elite lines is generally much higher than the original wild (landrace) accessions. The elite lines can be used directly as crop plant or can be used to produce single-cross F1 hybrids.

In a more preferred embodiment of the hybrid method of the invention, it further comprises an additional step (c) in which those hybrids harvested in step (b) showing an inactivation of a gene which encodes for a protein, wherein said protein comprises an amino acid sequence with at least 60%, 62%, 65%, 70%, 75%, 80%, 85%, 90%, 91%, 92%, 93%, 94%, 95%, 96%, 97%, 98%, 99%, or 100% sequence identity with SEQ ID NO: 1, are selected by human intervention.

Another aspect of the present invention relates to a plant or part thereof, a reproductive or propagating plant material, or a plant cell obtained by the hybrid method of the invention.

Another aspect of the present invention relates to a method for producing the plant of the invention or part thereof, the reproductive or propagating plant material of the invention, or the plant cell of the invention, wherein said plant or part thereof, said reproductive or propagating material or said plant cell presents resistance to infection by PepMV or improved phenotype in terms of PepMV infection resistance compared to the wild type, from here onwards the introgression method of the invention, comprising:

a) Crossing a breeding plant of the invention or part thereof, a breeding reproductive or propagating plant material of the invention, or a breeding plant cell of the invention with a second plant;
    b) selecting a progeny plant resulting from the crossing in step a) having an introgression from the breeding plant of the invention or part thereof, the breeding reproductive or propagating plant material of the invention, or the breeding plant cell of the invention associated with resistance to PepMV or improved phenotype in terms of PepMV infection resistance;

c) selfing and/or backcrossing said progeny plant selected in step (b) using said breeding plant of the invention or part thereof, a breeding reproductive or propagating plant material of the invention, a breeding plant cell of the invention line or a second plant as in (a) as a parent;

d) selecting a progeny plant resulting from the crossing in step c) having an introgression from the breeding plant of the invention or part thereof, the breeding reproductive or propagating plant material of the invention, or the breeding plant cell of the invention associated with resistance to PepMV or with improved phenotype in terms of PepMV infection resistance; and e) repeating said steps of selfing and/or backcrossing and selection of steps (c) and (d) to provide a plant breeding line essentially homozygous for said introgression, wherein at least one selection as performed in steps (b) or (d) is performed by marker-assisted selection, wherein the introgression comprises a mutation in a gene which encodes a protein, wherein said protein comprises an amino acid sequence with at least 60%, 62%, 65%, 70%, 75%, 80%, 85%, 90%, 91%, 92%, 93%, 94%, 95%, 96%, 97%, 98%, 99%, or 100% sequence identity with SEQ ID NO: 1, and wherein said mutation leads to an inactivation of the gene.

A used herein the term "introgression" is intended to mean introduction of a genetic determinant into a plant not carrying the genetic determinant by means of crossing and selection as from the first generation in which the trait becomes visible or detectable. For a dominant trait, selection may start as soon as the progeny of an F1 of a cross between a plant exhibiting the trait and a plant without the trait begins to segregate for the said trait (e.g., the F2 or first backcross [BC1] generation). For a recessive trait this is possible also from the F2 on. Alternatively, and specially for a polygenic trait, selection can be performed with molecular markers linked to the trait. Marker assisted selection may be carried out in any generation or population that may comprise plants carrying the marker.

The term "crossing" as used herein refers to the fertilization of female plants (or gametes) by male plants (or gametes). The term "gamete" refers to the haploid reproductive cell (egg or sperm) produced in plants by mitosis from a gametophyte and involved in sexual reproduction, during which two gametes of opposite sex fuse to form a diploid zygote. The term generally includes reference to a pollen (including the sperm cell) and an ovule (including the ovum). "Crossing" therefore generally refers to the fertilization of ovules of one individual with pollen from another individual, whereas "selfing" refers to the fertilization of ovules of an individual with pollen from the same individual. When referring to crossing in the context of achieving the introgression of a genomic region or segment, the skilled person will understand that in order to achieve the introgression of only a part of a chromosome of one plant into the chromosome of another plant, it is required that random portions of the genomes of both parental lines will be recombined during the cross due to the occurrence of crossing-over events in the production of the gametes in the parent lines. Therefore, the genomes of both parents must be combined in a single cell by a cross, where after the production of gametes from said cell and their fusion in fertilization will result in an introgression event.

The term "backcross" refers to the process wherein the plant resulting from a cross between two parental lines is crossed with one of its parental lines, wherein the parental line used in the backcross is referred to as the recurrent parent. Repeated backcrossing results in the genome becoming more and more homozygous or inbred.

Another aspect of the present invention relates to a plant or part thereof, a reproductive or propagating plant material, or a plant cell obtained by the introgression method of the invention, characterized in that it comprises a gene which encodes for a protein, wherein said protein comprises an amino acid sequence with at least 60%, 62%, 65%, 70%, 75%, 80%, 85%, 90%, 91%, 92%, 93%, 94%, 95%, 96%, 97%, 98%, 99%, or 100% sequence identity with SEQ ID NO: 1 and said gene has been inactivated.

All the definitions of terms previously described in relation to other aspects of the present invention are equally valid for all aspects and the embodiments of the present invention.

DESCRIPTION OF THE DRAWINGS

FIG. 4—Mapping of the mutation conferring resistance to PepMV in 2F531. (A) Susceptibility of $BC_1F_1$ to PepMV-H30, compared to WT and 2F531: viral load accumulation (ng of viral RNA/100 ng total RNA), at 16 days post inoculation (dpi); averages and SD of 8 replicates of 3 plants each. a and b indicate levels of PepMV accumulation significantly different (p<0.05, LSD test). (B) Phenotyping of $BC_1F_3$: Histogram of $BC_1F_3$ families regarding their % of susceptible individuals. (C) Manhattan plot representing the difference in allelic frequencies between the WT and R pools (y axis), in all detected variants along the tomato chromosomes according to the reference genome (Heinz 1706, SL2.50). The dotted line shows the threshold for difference in allelic frequencies higher than 0.7, indicative of association with resistance. (D) Genetic map and association analysis of SNPs in the candidate region of Chromosome 2: Linkage map of 12 markers in the candidate region after segregation analysis of 200 $BC_1F_2$ individuals, genetic distances in cM (center); and probability plot of loss-of-susceptibility being associated with the markers, represented as LOD score (scale on top of the graph, right).

FIG. 5—Number of paired reads mapping to candidate genes. Number of normalized paired reads after RNA-seq (Y axis) that mapped to each candidate gene, in 3 pools of six F2 plants each, whose offspring displays either the resistant (R) or the susceptible (WT) phenotype.

FIG. 6—Editing the SlOSCA4.1 gene using CRISPR/Cas9. (A) Schematic representation of the coding sequence of the wild type (WT) SlOSCA4.1 gene indicating the positions of the designed gRNAs used for gene editing by CRISPR/Cas9 and the edited gene slosca4.1_2 sequenced from edited plants, with a 1192 bp deletion respect to the WT gene. (B) PepMV-symptom expression in WT and slosca4.1_2-knockout tomato plants infected (or not for the healthy control) with PepMV-H30. (C) Accumulation of PepMV-Sp13 in tomato WT plants and slosca4.1_2 knock-out mutants at 16 days post inoculation. Data are means and standard deviation from 6 infected plants. The asterisks indicate significant differences using the One-way ANOVA statistical test (*** $p < 0.001$).

EXAMPLES

Example 1

Example 1.1: Methods

Tomato Mutants Screening

Figure 1:
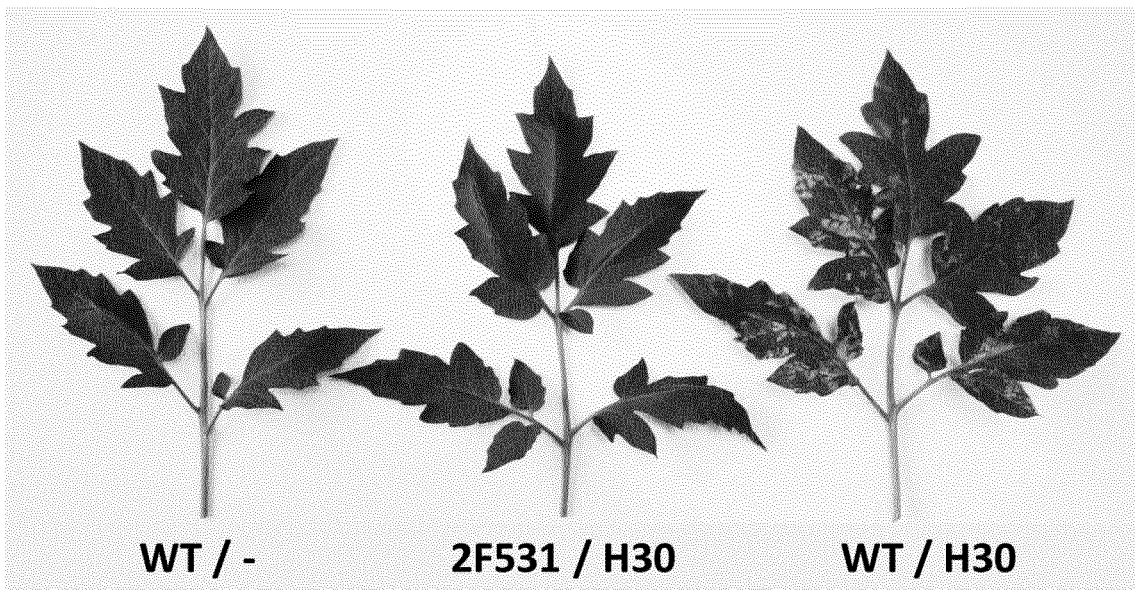
FIG. 1—Symptoms induced by PepMV-H30 in leaves of wild type and mutant tomato plants. Wild type (WT) and 2F531 mutant plants of the tomato cultivar M82 were inoculated (or non-inoculated (−) for the healthy controls) with the aggressive isolate PepMV-H30, which induces bright yellow mosaics in the leaflets of the infected plants. The picture was taken after 16 days post inoculation.

The mutant population consisted of 1,000 $M_2$ families supplied after treating seeds of the tomato cv. M82 with ethyl methanesulfonate (EMS). Twenty-five plants per family were seeded in a nursery (Murcia, Spain) and 33 days after seeding transplanted to greenhouses (Murcia, Spain) with windows and entrances protected with anti-thrips mesh. WT tomato cv. M82 plants were included as susceptible controls and for the border lines. Plant density was 4 plants per square meter. Plants were inoculated with the aggressive isolate PepMV-KLP2 (Agüero et al., 2018, Front Plant Sci 9, 1-12) the same day of transplantation. *Nicotina benthamiana* plants were used to propagate the inoculum: 14 days after inoculation (dpi), symptomatic leaves above the inoculated ones were harvested, blended with 30 mM phosphate buffer pH 8 to a concentration of 100 g/L, and preserved at −80° C.; for inoculations, this stock was diluted 5 times. Tomato plants were sprayed at high pressure with a suspension of carborundum powder (0.037 mm particle size; 10 g/L) in the inoculum solution. We used a total of 28 L of diluted inoculum solution for the whole tomato mutant population. A second round of inoculation was performed 28 days later, to ensure infection. Each $M_2$ µlant was scored for symptoms 42 days after the initial inoculation. A 0-2 symptom severity scale was defined as follows: 0, no symptoms; 1, sporadic bright yellow spots in newly emerged leaves; 2, bright yellow mosaic affecting all newly emerged leaves. Plants scoring 0 and 1 were selected. To check the association of symptoms with actual infection, PepMV detection was performed in 10 plants per family; we used molecular hybridization in tissue prints of petioles cross sections as in Marco et al. (2003, Phytopathology 93, 844-852). Crops were managed following conventional practices, except that extreme hygiene measures were adopted for personnel working in the greenhouses. Once evaluated, fruits from plants with mild or no symptoms were harvested and seeds extracted, thus preserving over 600 $M_3$ families.

In a second round of selection, 10-12 plants per $M_3$ family were evaluated; seeds were disinfected with 4% $H_2O_2$ for 30 minutes to eliminate contaminating PepMV, then sown in 40 seedling trays, inoculated and grown in an experimental greenhouse (CEBAS-CSIC, Murcia, Spain). The viral isolate used for inoculations was PepMV-H30 which, like PepMV-KLP2, induces bright yellow mosaics but has a more stable infection phenotype (Agüero et al., 2018, Front Plant Sci 9, 1-12). In this case, inoculum was produced in tomato plants (cv. Moneymaker) and mechanical inoculations were performed manually as in Agüero et al. (2018, Front Plant Sci 9, 1-12) at 21 days after seeding. Plants were reinoculated 14 days after the first inoculation. Symptom display was annotated at 25 dpi, recording the percentage of symptomatic plants per family. After evaluation, 3-6 plants of the selected families were transplanted to coconut fiber sacs and grown in greenhouses (Finca "La Matanza", CEBAS-CSIC, Murcia, Spain) under standard cultivation conditions until fruit maturation. For selected plants, controlled pollinations were conducted to obtain two rounds of selfings ($M_4$ and $M_5$ seed).

Measuring Viral Load in 2F531 Plants

Four PepMV isolates were assayed on WT and 2F531 ($M_5$ seed) plants: PepMV-Sp13 and PepMV-H30 belonging to the EU strain, and PepMV-PS5 and PepMV-KLP2 to the CH2 strain. PepMV-Sp13 and -PS5 are attenuated isolates inducing mild symptoms, while PepMV-H30 and -KLP2 are aggressive isolates (Agüero et al., 2018, Front Plant Sci 9, 1-12). Inocula were revived in *N. benthamiana* plants following standard practices. Three to four replicates of 3 tomato plants per genotype were inoculated with each virus or viral isolate. In all cases, plants with 2 true leaves were inoculated mechanically as previously described (Gómez et al., 2009a, J Virol 83, 12378-12387) and sampling was carried out at 16 dpi. Plants were grown in 1.1 L pots filled with a mix of peat and coconut fiber (2:1) in a crystal greenhouse (CEBAS-CSIC) with climatic control (day temperature set up at 24-25° C., night temperature at 16-18° C., 16 h of light). Viral RNA quantification was performed after extracting total RNA. All leaves from plants from each replicate were harvested and homogenized in a blender with 4 mL of TNA buffer per g of plant tissue (TNA: 2% SDS, 100 mM Tris HCl pH 8, 10 mM EDTA pH 8); 500 µl of the homogenates were sampled and mixed with the same amount of TRI-Reagent® (RNA Isolation Reagent, Sigma Chemical Co, USA); RNA extraction was carried out according to the manufacturer's instructions. The final precipitate was dissolved in 50 µl of sterile RNase free water and any residual DNA was eliminated by treatment with the TURBO DNA-free TM kit (Invitrogen, USA), according to the manufacturer's protocol. Quantity of RNA was estimated in a Nano-Drop® One (Thermo Scientific, USA). RT-qPCR was used for quantification of viral RNA. Standard curves were generated for each of the different viruses assayed, with 1:10 serial dilutions of a viral RNA of known concentration. The KAPA SYBR® FAST Universal One-Step RT-qPCR Kit (KAPA Biosystems, USA) was used, with 2 µl of the purified viral RNA dilution or extracted plant RNA, in a reaction volume of 20 µl, and with specific primers (Gómez et al., 2009a, J Virol 83, 12378-12387).

Three technical replicates per biological replicate were analyzed using a thermocycler StepOnePlus (Applied Biosystems, USA).

Serial Passaging Experiment

Figure 3:
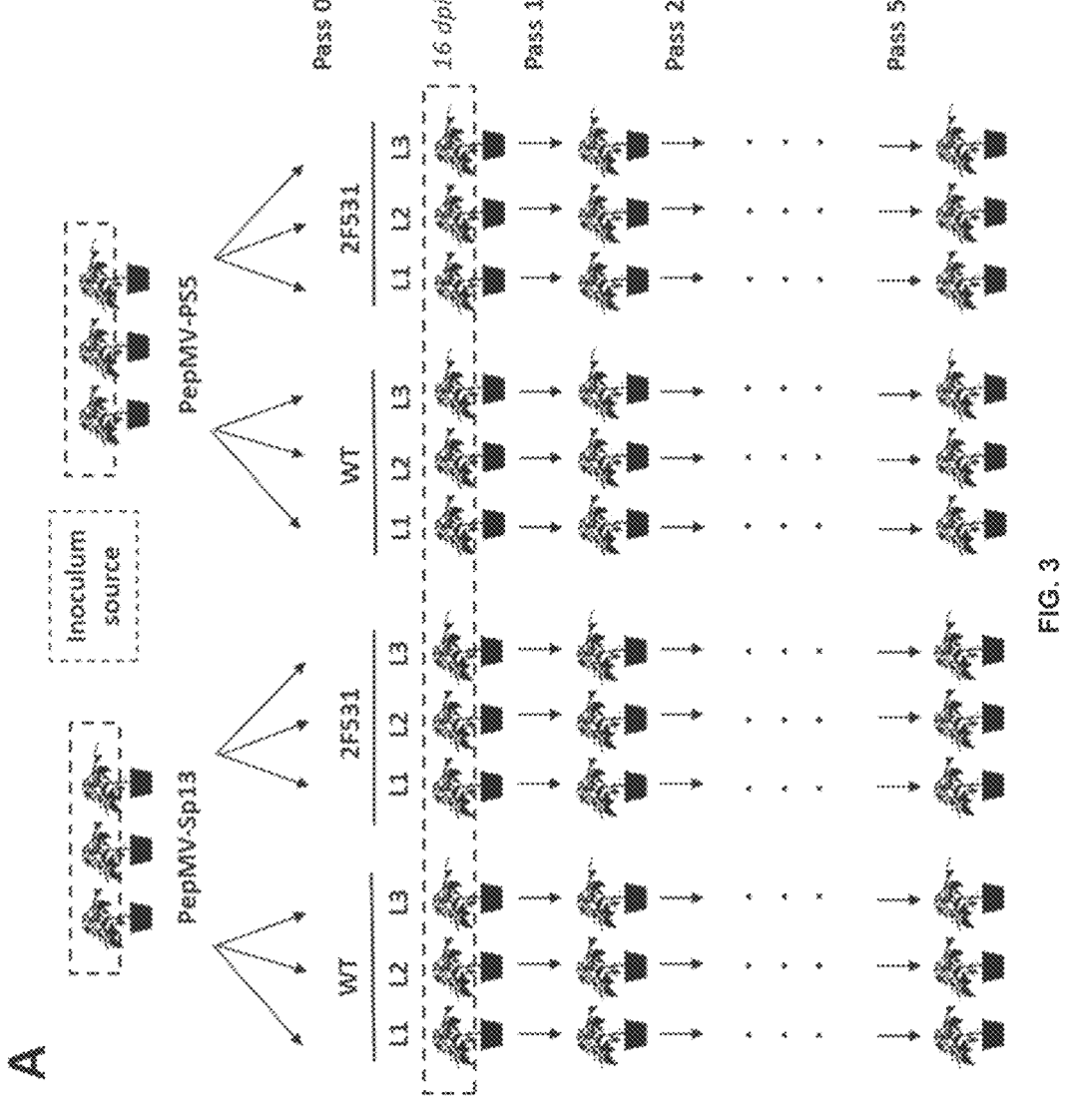
FIG. 3—Durability of the resistance of mutant 2F531. Up to five passages of two PepMV isolates were carried out in WT and mutant plants to estimate the probability of resistance breaking: (A) Scheme of the set up for stablishing 6 lineages of PepMV-Sp13 and 6 of PepMV-PS5 in WT and 2F531 plants. (B) Viral load evolution along the experiment ($\log_{10}$ ng of viral RNA/100 ng total RNA, at 16 days post inoculation (dpi)), for the isolates PepMV-Sp13 (top) and PepMV-PS5 (bottom).

The stability of resistance to PepMV in 2F531 plants was characterized in a serial-passaging experiment. Two plant (2F531 and WT) and 2 virus (PepMV-Sp13 and PepMV-PS5) genotypes were included in this experiment. $M_5$ seeds were used for 2F531. Three plants per genotype and per PepMV isolate were used to establish 12 lineages (FIG. 3A). Initial inocula for both isolates were first refreshed in WT plants, quantified as described above, and prepared for passage 0 to a concentration of approximately 107 virus copies/ng of total RNA. Fifty μL of inoculum was used to mechanically inoculate each of the founder plants of each lineage at the 2 true leaves stage, and then 5 successive passages were carried out; for that, 4 discs of 10.7 mm were taken from the second leaf above the inoculated one at 16 dpi, and used as the new inoculum source for the next passage on that lineage (FIG. 3A). Another 4 discs from the same leaf were kept frozen at −80° C. for quantifying viral load as described above. All the plants were grown in 1.1 L pots filled with a mix of peat and coconut fiber (2:1), in a crystal greenhouse (CEBAS-CSIC) with climatic control (day temperature set up at 24-25° C., night temperature at 16-18° C., 16 h of light).

Mapping Populations and Phenotyping

Controlled pollinations were conducted to obtain the backcross to M82 (BC$_1$F1). BC$_1$F2 was obtained by controlled selfing of BC$_1$F1. Two-hundred and four BC$_1$F$_2$ individuals were grown and used as the mapping population, and selfed to generate 204 BC$_1$F$_3$ progenies. In all cases, plants were grown in coconut fiber sacs in a PVC greenhouse (Finca "La Matanza", CEBAS-CSIC). The phenotyping value of any given BC$_1$F$_2$ was determined by analyzing the susceptibility to PepMV-H30 of 10-12 of its BC$_1$F$_3$ descendants. The methodology for this progeny test was similar to the one described previously for the second round of selection in the massive screening, except for re-inoculation, that took place at 7 dpi, and final scoring at 14 dpi.

Bulked Segregant Analysis and High Throughput Genotyping

Two bulks were generated, the WT bulk with 18 BC$_1$F$_2$ individuals whose BC$_1$F$_3$ displayed 100% of symptomatic descendants, and the R bulk with 18 individuals with 0% symptomatic descendants. Leaf tissue of each BC$_1$F$_2$ individual was used for nucleic acids extraction. Automated DNA extraction was performed following the Maxwell® CSC (Promega Corp., USA) protocol for "PureFood GMO and Authentification Kit for Food, Feed and Seed samples". Minor modifications were used to improve yield; namely, 60 mg of ground tissue as starting material, 600 μL of CTAB, 30 μL of Proteinase K, a 2 h incubation at 65° C., and a final volume of 80 μL. DNA was quantified with Qubit™ dsDNA BR Assay Kit in a Qubit® 2.0 fluorimeter (Life technologies, USA), and its quality checked by electrophoresis in 1% agarose and in a Nano-Drop® One. DNA of the selected individuals was pooled so that each of them was equally represented, and both pools were deep sequenced by Macrogen Inc. (South Korea). TruSeq DNA PCR-Free libraries were generated, with a fragment size of 350 pb, and run in a HiSeq®2500-High Throughput HORM (Illumina Inc., USA) with paired-end reads, to achieve a depth of coverage of around 50×. The raw data was analyzed as follows: Reads quality was tested with FastQC (http://www.bioinformatics.babraham.ac.uk/projects/fastqc/); reads mapping against the tomato reference genome (cv Heinz 1706, version SL2.50; http://solgenomics.net/organism/Solanum_lycopersicum/genome; Tomato Genome Consortium, 2012) was done with BWA aligner (Li and Durbin, 2009, Bioinformatics 25, 1754-1760); M82 sequence was retrieved from public databases (Bolger et al., 2014a, Nat Genet 46, 1034-1038). The program Freebayes (Garrison and Marth, 2012, ArXiv:1207.3907 [q-bio.GN]) was used for variant calling of both pools and M82; allelic frequencies were calculated in pools and M82 after filtering (criteria: available data in both pools, coverage equal or higher than 20 per sample, variant quality of at least 25, and total frequency of an allele lower than 0.9). Finally, the difference of allelic frequencies between pools was calculated, and represented as a Manhattan plot using R software. It was estimated that for a mendelian recessive mutation associated with the observed loss of function, such difference would be no less than 0.7.

RNA-Seq

The same 18 BC$_1$F$_2$ individuals per bulk were further subdivided in 3 replicates of 6 plants. Equivalent amounts of leaf tissue from each of the 6 plants per pool was used for RNA extractions as described above, except that the final RNA preparations were obtained using the kit Nucleo-Spin® RNA plant (Macherey-Nagel GmbH, Germany). The resulting RNA preps were evaluated using a Nano-Drop® One and an Agilent 2100 bioanalyzer (Agilent Technologies, USA). All the samples showed RNA integrity numbers above 7.4. The six pools were sequenced (Macrogen Inc.) following library construction with the kit TruSeq Stranded mRNA LT (Illumina Inc.), in the NovaSeq™ 6000 platform (Illumina Inc.) with 151 bp paired read reads. Raw data were trimmed (adapters and 10 nucleotides of the 5' end) with the program Trimmomatic (Bolger et al., 2014b), and filtered for quality (a minimum QC of 30 and a length of at least 70 bp) with FastQC. Reads were paired with BBMap (www.sourceforege.net/projects/bbmap), and then mapped against the reference genome using the MEM algorithm of BWA (Li and Durbin, 2009, Bioinformatics 25, 1754-1760), checking the quality of the mapping with Qualimap (bampc). Variant calling and calculation of allelic frequencies was performed as described for DNA re-sequencing. The number of reads that mapped to annotated genes was calculated with the function featureCounts of SubRead, its quality with DESeq2 and their normalization with rlog. DESeq2 allowed also to study the differential expression between the R and WT samples, considering two factors, genotype and replicate. Goseq was used for the enrichment analysis GO. Finally, the biological impact of the variants was predicted with SnpEff (Cingolani et al., 2012, SnpEff. Fly 5, 29-30).

CRISPR/Cas9 Editing

Three gRNAs complementary to the SlOSCA4.1 coding sequence were designed using the BreakingCas bioinformatics tool (Oliveros et al., 2016). The targeted sequences in SlOSCA4.1 were 5'-ACTTCAATTACGACGTCGCT-3' (SEQ ID NO: 7), 5'-CAGAGCTGCCGCCCTCAATA-3' (SEQ ID NO: 8), and 5'-ATAAGGCTGTCCAGGACCTC-3' (SEQ ID NO: 9). Sense and antisense oligonucleotides (Integrated DNA Technologies, Inc.) were annealed and cloned into the pDIRECT_22C (Addgene ref. #91135) binary plasmid following the protocol described in Čermák et al. (The Plant cell, 2017 29(6), 1196-1217). The resulting plasmid was used to transform *Agrobacterium tumefaciens* strain GV3101, which on its turn was used to transform explants of tomato cv. Micro-Tom following the protocol described in Van Eck et al. (Methods in molecular biology, 2006, 343, 459-473). Plants rooted in selective medium were transferred to substrate and acclimatized in growth chambers. To check if edition of SlOSCA4.1 took place in TO plants, the targeted region within the gene was PCR-amplified by direct tissue PCR using the Phire Tissue direct PCR kit (Thermo Scientific) following the manufacturer's specifications, and Sanger sequenced. Edited plants were selfed to obtain the T1 seed. T1 plants grown in substrate were genotyped, selecting those that had the mutation in homozygosis.

Example 1.2: Loss-of-Susceptibility to PepMV in a Collection of Tomato Mutants A screening was conducted on a population of 25,000 tomato mutants from 1,000 M2 families. Mutant plants were inoculated with an aggressive PepMV isolate which induces obvious bright yellow mosaics. Symptom severity was scored for each plant according to a 0-2 scale, were 0 is absence of symptoms, 1 is sporadic bright yellow spots in newly emerging leaves, and 2 is bright yellow mosaic affecting all newly emerged leaves (FIG. 1). Aggressive symptoms (score 2) appeared in 97.5% of the plants, which were recorded as susceptible. There were plants scoring 0 or 1 in 379 families. A subpopulation of symptomatic and asymptomatic plants was tested for PepMV infection, revealing a perfect correlation between infection and symptoms display. One to 4 plants per family scoring 0 or 1 were selected and selfed, giving rise to more than 600 $M_3$ families. From these, 10 to 12 individuals from each of 453 $M_3$ families were inoculated with PepMV, and symptom scoring was again annotated. Family 2F531 showed 100% of symptomless plants, pointing to a homozygous mutation causing loss-of-susceptibility to PepMV; plants of this family were selfed to generate $M_4$ seeds and backcrossed to the wild type accession M82 to obtain $BC_1F1$. From now on, we will refer to the loss-of-susceptibility phenotype of these plants as resistance.

Tomato plants bearing the inactivated gene of the invention display no phenotypic differences relative to the wild type, other than the resistance to infection by PepMV or improved phenotype in terms of PepMV infection resistance. Neither plantlets (FIG. 6B) nor fully grown plants of mutants 2F531 or the slosca4.1_2-knockout could be distinguished from the WT plants in absence of infection by PepMV: they have similar determinate growth habit, size, color and shape of leaves, as well as fruits appearance, number or setting, and seed production (yield and germinability) indicating, that the mutation does not alter the fitness of the tomato plants.

Breadth and Durability of Resistance in Mutant 2F531

Figure 2:
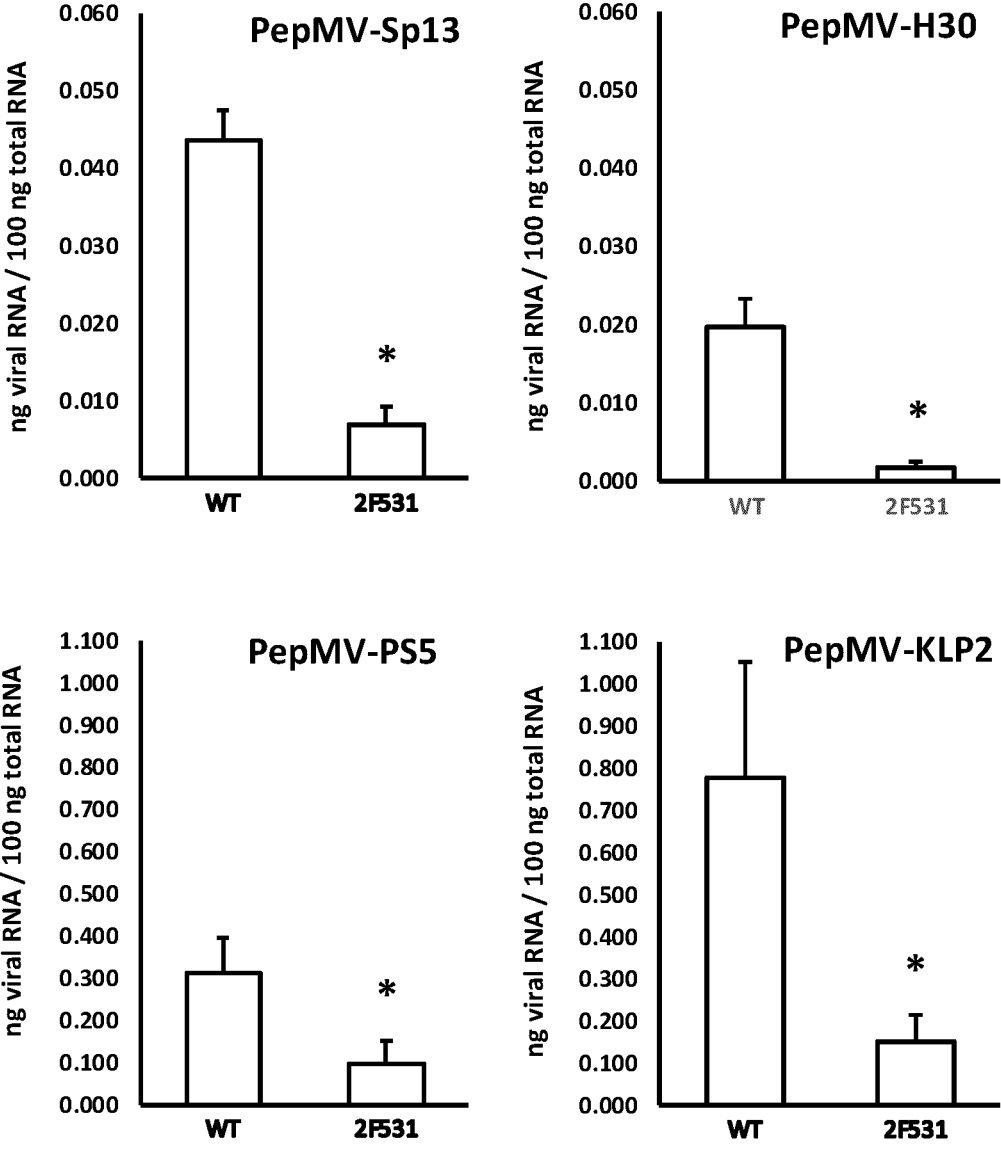
FIG. 2—Resistance of mutant 2F531 tomato plants to PepMV isolates from different strains. Viral load was measured by RT-qPCR using specific primers and referred to a calibration curve for absolute PepMV RNA quantification. A sharp decrease in PepMV accumulation was observed for 2F531 with respect to WT plants. PepMV isolates were: PepMV-Sp13, -H30 (EU strain), -PS5 and -KLP2 (CH2 strain). Average and SD of 4 replicates of 3 plants each. Total RNA was extracted at 16 days post inoculation. * indicates significant differences (p<0.05, T Student test).

PepMV accumulation in wild type (WT) and 2F531 plants was compared after inoculation with PepMV-Sp13, PepMV-H30 (both belonging to the EU strain), PepMV-PS5 or PepMV-KLP2 (belonging to the CH2 strain). There was a sharp and significant decrease in viral load in the mutant with respect to the WT plants for all four isolates (FIG. 2), which was more pronounced for the EU (9 to 10-fold) than for the CH2 isolates (3 to 5-fold), and also sharper for the aggressive (PepMV-H30 and -KLP2) than for the mild (PepMV-Sp13 and -PS5) isolates.

Resistance durability is key for deploying sustainable pathogen control strategies in the field. To test if PepMV could easily overcome the 2F531 resistance, a passaging experiment was carried out. After initial inoculation with PepMV-Sp13 or PepMV-PS5, three viral lineages were set up on plants of each M82 or 2F531 genotypes, and 5 successive passages were carried out (FIG. 3A). Viral load was measured for each passage. For PepMV-PS5 passages, viral load fluctuated but it was always smaller (almost one order of magnitude in most cases) in the 2F531 than in the WT plants (FIG. 3B). For PepMV-Sp13, viral load fluctuations with passaging were more pronounced and, indeed, by the $3^{rd}$, $4^{th}$ and $5^{th}$ passages, viral populations in each of the 2F531 lineages, respectively, became almost extinct (FIG. 3B).

Mapping-by-Sequencing the Mutation Associated to Loss-of-Susceptibility to PepMV $BC_1F_1$ plants showed similar PepMV accumulation and symptoms than WT plants (FIG. 4A), indicating that the 2F531 resistance has a recessive nature. $BC_1F_1$ plants were selfed to obtain over 200 $BC_1F_2$ plants, which were grown, selfed to obtain their $BC_1F_3$ progenies, and individually sampled for DNA and RNA extractions. Two hundred and four $BC_1F_3$ families where phenotyped by inoculating 12 plants per family with PepMV. In 50 and 54 $BC_1F_3$ families, respectively, all individuals were either resistant or susceptible, while within-family segregation was observed in 100 cases (FIG. 4B). These frequencies fit almost to perfection to the expected gene segregation in a model in which resistance is monogenic and recessive ($\chi2$ statistic, 2 df=0.23; $\alpha>0.001$).

Bulked Segregant Analysis (BSA) coupled to High Throughput Sequencing (HTS) was adopted to map the mutation associated with PepMV resistance. Two bulks were built, with 18 $BC_1F_2$ individuals in the R pool (i.e., 0% susceptible plants in $BC_1F_3$) and another 18 $BC_1F_2$ individuals in the WT pool (i.e., 100% susceptible plants in $BC_1F_3$). Pooled DNAs were sequenced for each bulk to a 50×depth. After quality filtering and alignment onto the reference genome (Heinz 1706, SL2.50), 99% of the reads could be mapped, 78% of them having a quality score MAPQ>57. Variant calling against the reference genome detected 1,285,278 variants after filtering for low coverage. Most of the variants could be attributed to natural polymorphisms between M82 and Heinz 1706, and only 6,302 (0.49%) to the EMS-induced mutagenesis; this indicates an approximate rate of 1 mutation each 150 Kbp in mutant 2F531. Allelic frequencies in each pool were calculated for all variants. The difference in allelic frequencies was greater than 0.7 for 10 SNPs and 1 Insertion/Deletion located at the distal end of chromosome 2, indicating an association between variant alleles and pool type (FIG. 4C). These 11 variants span a region of 2.02 Mb, from position 45,135,056 to 47,155,034; five of the mutations are located in annotated genes. This region includes 448 other variants of low coverage and encompasses 145 annotated genes.

To refine gene mapping, an analysis of recombination was carried out. Twenty-four SNPs identified inside or adjacent to the genomic region of interest were selected and analyzed in 200 $BC_1F_2$ individuals; only 12 of the markers segregated in the population. A linkage map was constructed for those markers and an association analysis was carried out to correlate marker genotypes and susceptibility. FIG. 4D displays the genetic map and the probability density along it and illustrates the strong association of resistance with markers C18 and C19. An analysis of recombinants further indicates that the loss-of susceptibility to PepMV is only displayed by individuals with alternative alleles in homozygosis at the region framed by C16 and C20, spanning 734,632 bp. Within this region, the BSA-HTS analysis identified 4 variants; the predicted functional effect of these variations was low to moderate except for mutation A to T at nucleotide position 1803 within the only Solyc02g083430 exon, which corresponds to position 1660 within the Solyc02g083430 main open reading frame. The protein encoded by Solyc02g083430 has 831 amino acids, and the mutation affects lysine at position 554, introducing a premature stop codon instead.

To validate and complement the above data, an RNA-Seq analysis was carried out using pooled RNAs from the R and WT bulks. Transcripts were sequenced, mapped to the reference genome and filtered, variants were identified, and allelic frequencies between pools were compared. Again, the only loci where allelic frequencies differed by more than 0.7 were located in the same genomic region as previously found, and variants were specifically detected in three loci, Solyc02g081200, Solyc02g082660 and Solyc02g083430. Some new SNPs could be identified in the area, but with low coverages. When comparing the number of readings mapping to each of the three RNA-Seq candidates for the R vs the WT pool (FIG. 5), differences were observed for Solyc02g083430; although these were not statistically significant, readings for Solyc02g083430 seemed to be less for the resistant than for the susceptible bulk, in agreement with the nature of the mutation observed for this gene. On the other hand, a gene ontology (GO) enrichment analysis identified 27 over-represented GO terms. Almost 9% of the deregulated genes are related to ATPase complexes within the category of cellular component. Within the molecular function category, ATP binding (GO: 0005524), Aspartic-type endopeptidase activity (GO: 0004190) and Oxidoreductase activity (GO: 0016491) were the most enriched. Finally, within the biological function category, only two enriched biological processes were identified: Response to wounding (GO: 0009611) and Alcohol metabolic process (GO: 0006066).

Solyc02g083430 Encodes SlOSCA4.1, a Protein Involved in Vacuolar Trafficking and Member of the Hyperosmolality-Gated Calcium-Permeable Channel 1 (OSCA) Family The protein encoded by Solyc02g083430 (genomic sequence SEQ ID NO: 4), SEQ ID NO: 1, has 3 conserved domains: A transmembrane domain that is part of a calcium permeable cation exchange channel 1 (Csc1_N) activated by physical signals such as osmotic stress; a phosphate transporter domain, predicted as cytosolic (PHM7_cyt); and a region of 7 transmembrane domains that are part of a putative phosphate transporter (RSN1_7TM) (Zhu et al., 2008, Nat Genet 40, 854-861). The premature introduction of the stop codon at amino acid 554 results in the loss of much of the RSN1_7TM transmembrane domain, which could cause the total or partial loss of the protein function, resulting in the mutant phenotype. Its closest *Arabidopsis* ortholog encodes AtOSCA4.1, which belongs to the hyperosmolality-gated/mechanically activated calcium-permeable channels (OSCA) family (Yuan et al., 2014, Nature 514, 367-371) and with which it shares 69% amino acid identity. As in *Arabidopsis*, the tomato OSCA4.1 (SlOSCA4.1) belongs to a small family composed of 12 members phylogenetically organized in the same four clades as in *Arabidopsis*. The AtOSCA4.1 has been clearly identified as a vacuolar sorting factor in two independent reports (Fuji et al., 2007, Plant Cell 19, 597-609; Delgadillo et al., 2020, PNAS 117, 9884-9895). A further search for orthologs of the protein encoded by the gene Solyc02g083430, in agricultural important species, with similar structural organization resulted in two sets of proteins: one extremely conserved inside the Solanaceae with a minimum identity of 91.29% across the whole protein (Table 1); and a second one highly conserved outside Solanaceae (Table 2) with a minimum identity of 62.77% across the whole protein. The structural similarity and domain distribution of both sets of proteins, indicated that the proteins must have a conserved function to the protein encoded by Solyc02g083430.

Editing SlOSCA4.1 in Tomato Cv. Micro-Tom Confirms its Proviral Function for PepMV To confirm the implication of SlOSCA4.1 in PepMV susceptibility, we used the genome editing technology CRISPR/Cas9 to produce tomato cv. Micro-Tom mutants in the Solyc02g083430 locus. Guide RNAs were designed targeting sequences at the beginning of the only Solyc02g083430 exon. Homozygous mutations were observed in individual plants of the T1 generation (FIG. 6A), which were inoculated with PepMV. An infection phenotype similar to that of mutant 2F531 plants was observed: no disease symptoms were seen in edited plants (FIG. 6B) and PepMV accumulation was significantly reduced in the mutant compared to the WT plants (FIG. 6C), thus validating the starting hypothesis.

TABLE 1

Orthologs of SEQ ID NO: 1 in Solanaceae species

| Species (Solanaceae) | % id |
|---|---|
| *Nicotiana_benthamiana_1* | 91.29 |
| *Nicotiana_benthamiana_2* | 92.27 |
| *Capsicum_annuum_cv* | 93.98 |
| *Capsicum_annuum_glabriusculum* | 94.26 |
| *Capsicum_annuum_zunla* | 94.38 |
| *Solanum_melongena* | 93.98 |
| *Solanum_lycopersicum* | 100.00 |
| *Solanum_pimpinellifolium* | 100.00 |
| *Solanum_pennellii* | 98.32 |
| *Solanum_tuberosum* | 97.56 |

TABLE 2

Orthologs of SEQ ID NO: 1 in non-Solanaceae species

| Species (Non Solanaceae) | % id |
|---|---|
| *Musa_acuminata* | 65.04 |
| *Zea_mays* | 62.96 |
| *Oryza_sativa_Indica* | 62.77 |
| *Triticum_aestivum* | 63.12 |
| *Brassica_rapa* | 69.33 |
| *Brassica_rapa_2* | 62.90 |
| *Daucus_carota* | 75.55 |
| *Actinida_chinensis* | 76.78 |
| *Sesamum_indicum* | 79.34 |
| *Olea_europaea* | 78.16 |
| *Solanum_lycopersicum* | 100.00 |
| *Coffea_canephora* | 80.37 |
| *Phaseolus_vulgaris* | 71.73 |
| *Glycine_max* | 70.85 |
| *Malus_domestica* | 72.29 |
| *Manihot_esculenta* | 73.79 |
| *Cucumis_sativus* | 71.11 |

Example 2

Example 2.1: Method

Protoplast Isolation and Inoculation

Protoplasts were isolated from leaves of WT and 2F531 mutant tomato plants by procedures described by Tan et al. (1987, *Plant cell reports*, 6(3), 172-175). Approximately 2 g of tomato leaves were harvested from both WT and 2F531 mutant and subjected to protoplast isolation. Each protoplast sample containing approximately $2\times10^6$ cells was inoculated with 50 μg of PepMV purified virion by PEG 4000 method and incubated 24 h at 26° C. with humidity and constant light in growth chamber. Protoplasts were sampled at 0, 17 and 24 h after infection. Total RNA was isolated from protoplast by Trizol reagent. Genomic DNA was removed from RNA samples, RNA was normalized and use for expression analysis by RT-qPCR. PepMV expression was standardized using elongation factor 1-alpha as endogenous gene.

Figure 7:
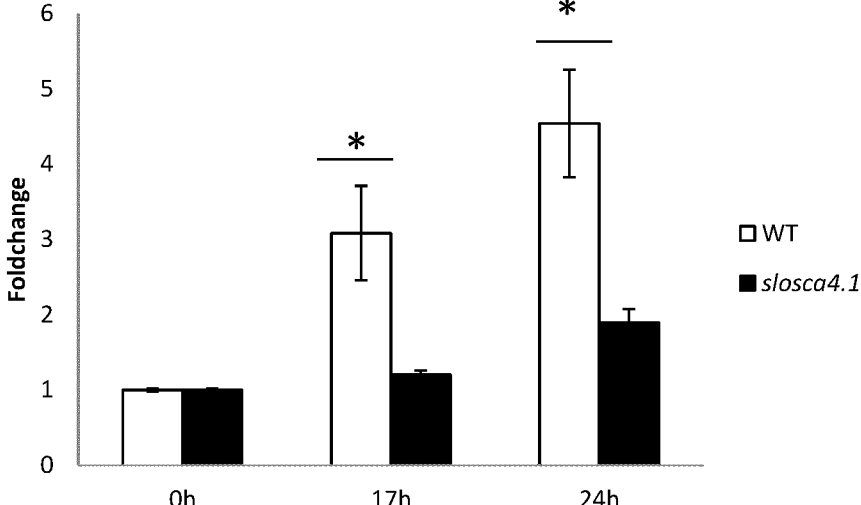
FIG. 7—Relative expression of PepMV in WT and 2F531 mutants leaves protoplasts. Protoplast from leaves of both WT and 2F531 mutants were infected with PepMV-SP13 purified virion. Relative expression of PepMV at 0, 17 and 24 hours post infection was analyzed by RT-qPCR. The expression at times 17 and 24 hours was relativized to time 0 hours. Data are the means and standard deviation of 8 experimental repetitions for the WT and 7 for the mutant. The asterisks indicate significant differences using the t statistical test ($p < 0.05$).

Example 2.2: Infection of Tomato WT and 2F531 Protoplasts with PepMV Confirms its Role in PepMV Replication within the Cell To complement data on the implication of SLOSCA4.1 in PepMV susceptibility and replication, we used leaves protoplasts of tomato cv. M82 both WT and mutant 2F531. Protoplast were isolated from leaves of WT and mutant plants, infected with PepMV purified virion and sampled at 0, 17 and 24 hours post infection. Viral expression was measured from total RNA by relative RT-qPCR using alpha elongation factor 1 (EF-1alpha) as endogenous gene for normalization. The results showed that relative accumulation of PepMV in protoplast from the mutant 2F531 plants was significantly reduced compared to the WT plants (FIG. 7), thus indicating that SIOSCA4.1 is involved in PepMV replication within the cell.

---

The invention claimed is:

1. A plant or part thereof, reproductive or propagating plant material or a plant cell showing resistance to infection by pepino mosaic virus (PepMV) or improved phenotype in terms of PepMV infection resistance, characterized in that it comprises a gene which encodes for a protein, wherein said protein comprises an amino acid sequence of SEQ ID NO: 2 and/or SEQ ID NO: 3.

2. The plant or part thereof, the reproductive or propagating plant material or the plant cell according to claim 1, wherein the plant or part thereof, the reproductive or propagating plant material, or the plant cell is not exclusively obtained by an essentially biological process.

3. The plant or part thereof, the reproductive or propagating plant material or the plant cell according to claim 1 belonging to the Solanaceae family.

4. The plant or part thereof, the reproductive or propagating plant material or the plant cell according to claim 1 belonging to *Solanum* sp., *Capsicum* sp., *Nicotiana* sp. or *Physalis* sp.

5. The plant or part thereof, the reproductive or propagating plant material or the plant cell according to claim 1 belonging to a species selected from the list consisting of: *Solanum lycopersicum, S. tuberosum, S. pennellii, S. pimpinellifolium, S. peruvianum, S. cheesmanii, S. galapagense, S. chilense, S. melongena, S. aethiopicum, S. quitoense, S. torvum, S. muricatum, S. betaceum, S. chmielewskii, S. arcanum, S, cornelliomulleri, S. habrochaiti, S. huaylasense,* *S. neorickii, S. dulcamara, S. lycopersicoides, S. sitiens, S. juglandifolium, S. ochranthum,* and *S. cheesmaniae.*

6. The plant or part thereof, the reproductive or propagating plant material or the plant cell according to claim 1, wherein the part of the plant is selected from the list consisting of: a leaf, a stem, a flower, an ovary, or a callus.

7. The plant or part thereof, the reproductive or propagating plant material or the plant cell according to claim 1, wherein the reproductive or propagating plant material is selected from a fruit, a seed, a tuber or a progeny, wherein the plant or part thereof comprises SEQ ID NO: 2 and/or SEQ ID NO: 3.

8. A method for producing a plant or part thereof, a reproductive or propagating plant material, or a plant cell according to claim 1, wherein said plant or part thereof, reproductive or propagating plant material, or plant cell shows resistance to infection by pepino mosaic virus (PepMV) or improved phenotype in terms of PepMV infection resistance, comprising:

a) Subjecting the plant or part thereof, the reproductive or propagating plant material, or the plant cell to mutagenesis either random or directed, and b) detecting a mutation in a gene which encodes a protein, wherein said protein comprises an amino acid sequence with at least 98% sequence identity with SEQ ID NO: 1, in the plant or part thereof, the reproductive or propagating plant material, or the plant cell, and wherein said mutation leads to an inactivation of the gene.

9. The method according to claim 8, wherein the random mutagenesis is achieved by contacting the plant or part thereof, the reproductive or propagating plant material, or the plant cell with a mutagenic agent.

10. The method according to claim 8, wherein the directed mutagenesis is achieved by homologous recombination-dependent gene targeting, antisense RNA, directed transposon insertion, virus induced gene silencing or genome editing techniques.

11. An agro-industrial product production method:
a) culturing the plant or part thereof, the reproductive or propagating plant material, or the plant cell, according to claim 1, and
b) harvesting the fruit, the seeds, the tubers or the edible part of the plant to produce the agro-industrial product.

12. A method for selecting plants with resistance to infection by PepMV or with improved phenotype in terms of PepMV infection resistance compared to the wild type comprising the steps of:
a) Detecting a gene which encodes for a protein wherein said protein comprises an amino acid sequence with at least 98% sequence identity with SEQ ID NO: 1, and
b) Determining if said gene of step a) is inactivated,
wherein an inactivated gene is indicative of resistance to infection by PepMV or improved phenotype in terms of PepMV infection resistance compared to the wild type.

13. A method for producing a hybrid of the plant or part thereof, of the reproductive or propagating plant material, or of the plant cell according to claim 1, wherein said hybrid shows resistance to infection by pepino mosaic virus (PepMV) or improved phenotype in terms of PepMV infection resistance, comprising:
a) Crossing the plant or part thereof, the reproductive or propagating plant material, or the plant cell with a second plant; and
b) Harvesting the hybrid progeny of said crossing.

14. A method for producing the plant or part thereof, the reproductive or propagating plant material, or the plant cell according to claim 1, wherein said plant or part thereof, reproductive or propagating plant material, or plant cell shows resistance to infection by pepino mosaic virus (PepMV) or improved phenotype in terms of PepMV infection resistance compared to the wild type, comprising:
a) Crossing a breeding plant or part thereof, a breeding reproductive or propagating plant material, or a breeding plant cell according to claim 1 with a second plant;
b) selecting a progeny plant resulting from the crossing in step a) having an introgression from the breeding plant or part thereof, the breeding reproductive or propagating plant material, or the breeding plant cell according to claim 1 associated with resistance to PepMV or improved phenotype in terms of PepMV infection resistance;
c) selfing and/or backcrossing said progeny plant selected in step (b) using said breeding plant or part thereof, a breeding reproductive or propagating plant material, a breeding plant cell line or a second plant as in (a) as a parent;
d) selecting a progeny plant resulting from the crossing in step c) having an introgression from the breeding plant or part thereof, the breeding reproductive or propagating plant material, or the breeding plant cell associated with resistance to PepMV or with improved phenotype in terms of PepMV infection resistance; and
e) repeating said steps of selfing and/or backcrossing and selection of steps (c) and (d) to provide a plant breeding line essentially homozygous for said introgression, wherein at least one selection as performed in steps (b) or (d) is performed by marker-assisted selection,
wherein the introgression comprises a mutation in a gene which encodes a protein, wherein said protein comprises an amino acid sequence with at least 98% sequence identity with SEQ ID NO: 1, and wherein said mutation leads to an inactivation of the gene.

15. The method according to claim 13, wherein the second plant in step (a) belongs to *Solanum* sp., *Capsicum* sp., *Nicotiana* sp. or *Physalis* sp.

16. The method according to claim 13, wherein the second plant of step (a) is an inbred line and the hybrid progeny of step (b) is a single-cross F1 hybrid.

17. The method according to claim 13, which further comprises an additional step (c) in which those hybrids harvested in step (b) showing an inactivation of a gene which encodes for a protein, wherein said protein comprises an amino acid sequence with at least 98% sequence identity with SEQ ID NO: 1, are selected by human intervention.

18. A plant or part thereof, a reproductive or propagating plant material, or a plant cell obtained by the method according to claim 13, wherein said plant or part thereof, reproductive or propagating plant material, or plant cell comprises a gene which encodes for a protein, wherein said protein comprises an amino acid sequence with at least 98% sequence identity with SEQ ID NO: 1 and said gene has been inactivated.

* * * * *